United States Patent
Parmar

(10) Patent No.: US 8,246,984 B2
(45) Date of Patent: Aug. 21, 2012

(54) FORMULATION OF INSOLUBLE SMALL MOLECULE THERAPEUTICS IN LIPID-BASED CARRIERS

(75) Inventor: Manjeet M. Parmar, North Vancouver (CA)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 708 days.

(21) Appl. No.: 12/094,836

(22) PCT Filed: Dec. 1, 2006

(86) PCT No.: PCT/US2006/061502
§ 371 (c)(1),
(2), (4) Date: Jul. 13, 2009

(87) PCT Pub. No.: WO2007/111720
PCT Pub. Date: Oct. 4, 2007

(65) Prior Publication Data
US 2009/0291129 A1 Nov. 26, 2009

Related U.S. Application Data

(60) Provisional application No. 60/742,954, filed on Dec. 6, 2005.

(51) Int. Cl.
*A61K 9/127* (2006.01)
(52) U.S. Cl. ............................................ 424/450
(58) Field of Classification Search .............. 424/450, 424/489
See application file for complete search history.

(56) References Cited

U.S. PATENT DOCUMENTS

| | | | |
|---|---|---|---|
| 4,515,736 A | 5/1985 | Deamer | |
| 4,610,868 A | 9/1986 | Fountain et al. | |
| 4,830,858 A | 5/1989 | Payne et al. | |
| 4,895,719 A | 1/1990 | Radhakrishnan et al. | |
| 4,937,078 A * | 6/1990 | Mezei et al. | 424/450 |
| 5,049,388 A | 9/1991 | Knight et al. | |
| 5,616,341 A | 4/1997 | Mayer et al. | |
| 6,423,345 B2 | 7/2002 | Bernstein et al. | |
| 6,680,068 B2 | 1/2004 | Campbell et al. | |
| 6,689,381 B2 | 2/2004 | Ashvar et al. | |
| 7,811,602 B2 * | 10/2010 | Cullis et al. | 424/450 |
| 2002/0058060 A1 * | 5/2002 | Kan et al. | 424/450 |
| 2004/0029902 A1 | 2/2004 | Singh et al. | |
| 2005/0191344 A1 | 9/2005 | Zalipsky et al. | |
| 2007/0060603 A1 | 3/2007 | Argade et al. | |

FOREIGN PATENT DOCUMENTS

| | | |
|---|---|---|
| EP | 0290296 | 3/1988 |
| WO | WO 03/063794 | 8/2003 |
| WO | WO 2004-046118 | 6/2004 |

OTHER PUBLICATIONS

West, Anthony R. Solid state chemistry and its application. Wiley, NY, 1988, pp. 358 & 365.*
Trosko, J.E., Mutation Research, 480-481, pp. 219-229, 2001.*

* cited by examiner

*Primary Examiner* — Gollamudi Kishore
(74) *Attorney, Agent, or Firm* — Klarquist Sparkman, LLP; Travis Young

(57) ABSTRACT

The present invention provides formulations containing at least one unsaturated amphiphilic lipid and an amphipathic or hydrophobic drug and methods of making these formulations. In particular, the present invention provides formulations of at least one unsaturated phospholipid and an amphipathic or hydrophobic pyrimidine drug, methods of making these formulations and the use of such formulations in a variety of contexts, including, for example, the treatment of proliferative disorders, such as tumors and cancers.

31 Claims, 11 Drawing Sheets

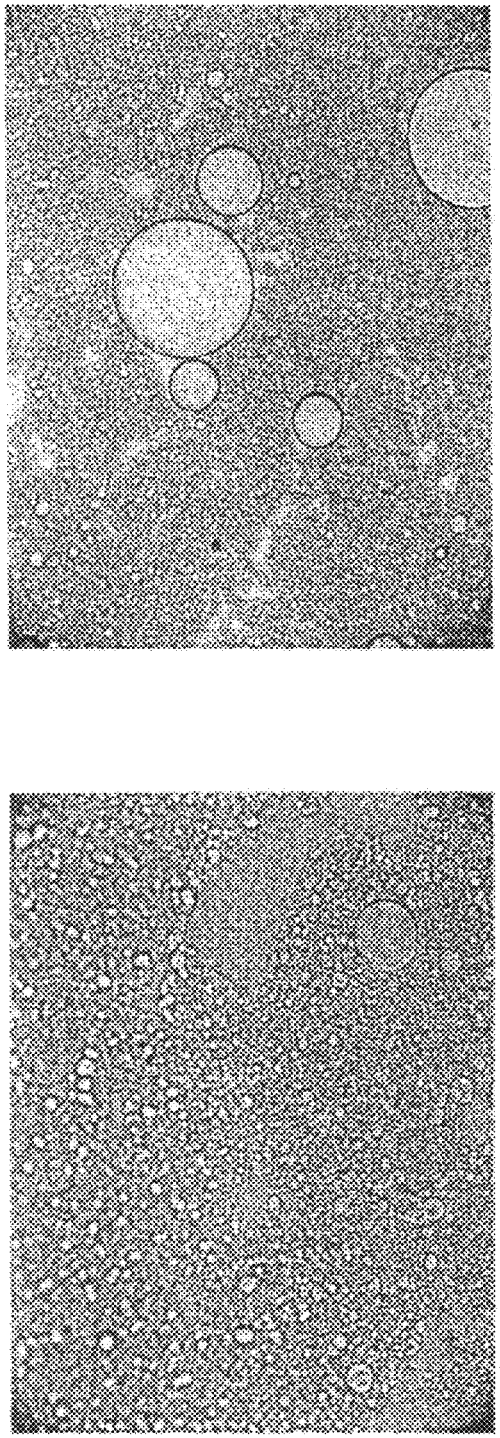
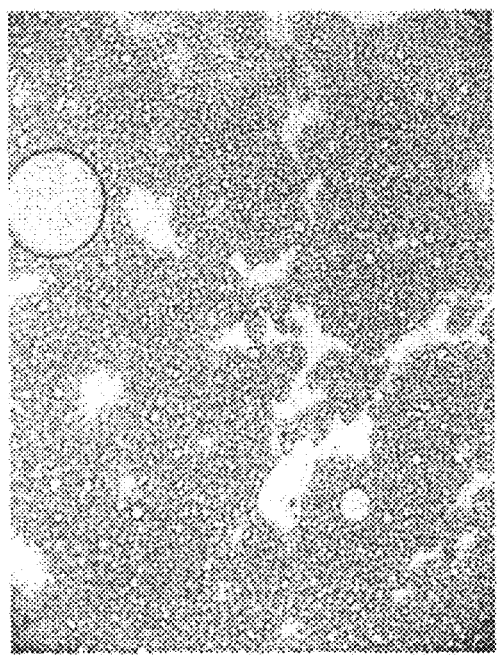
FIG. 2

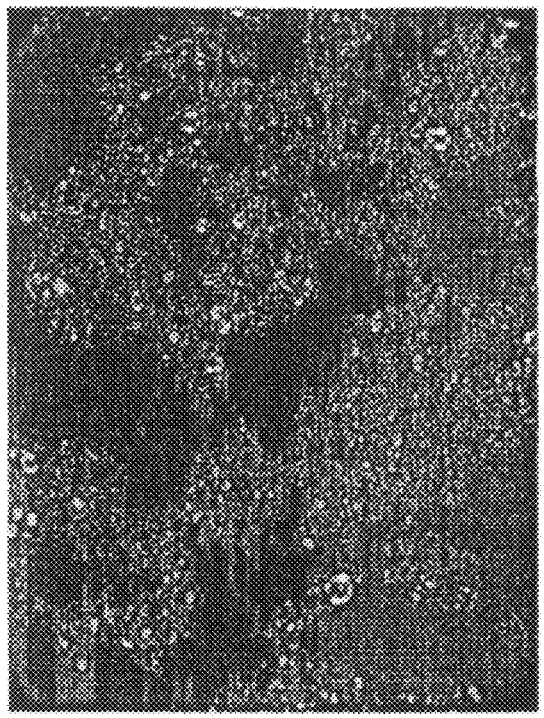
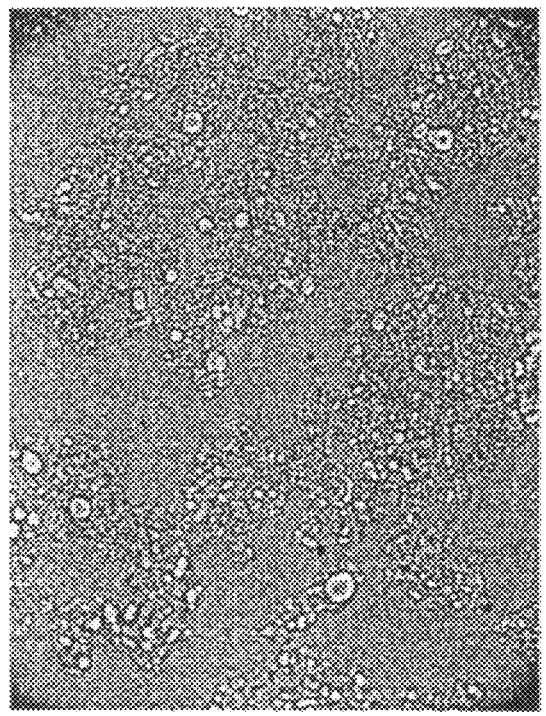
FIG. 3

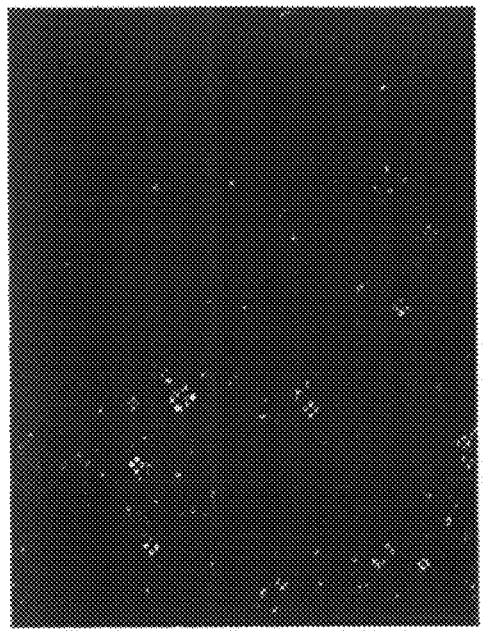
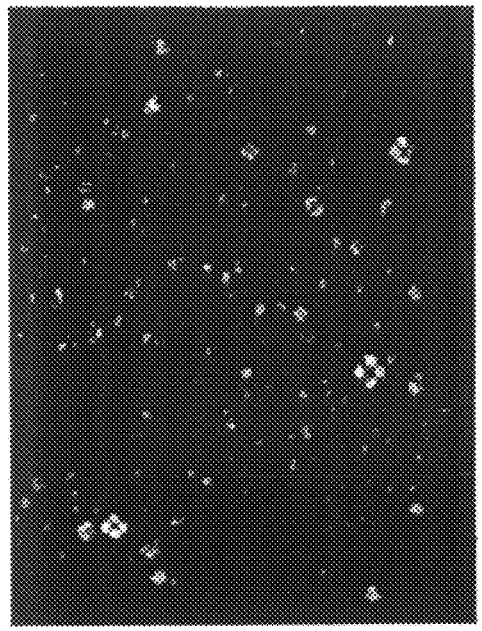
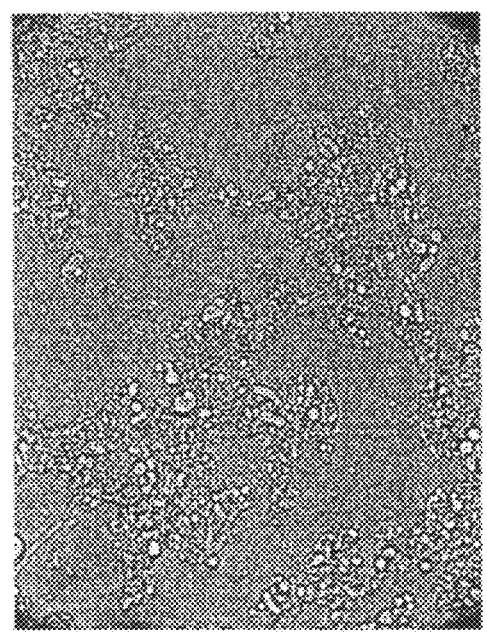
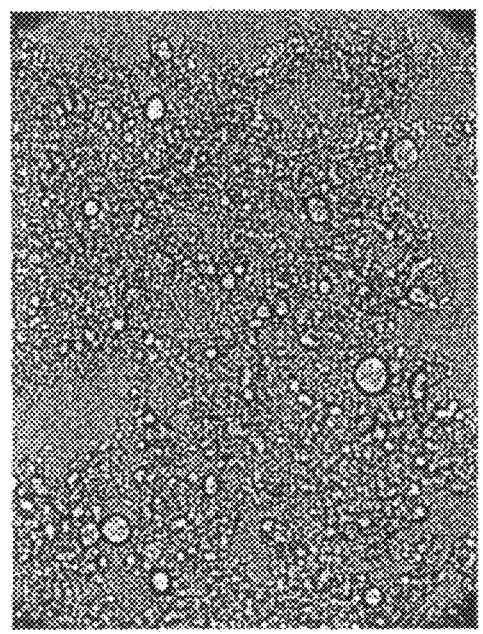
FIG. 4

FIG. 5
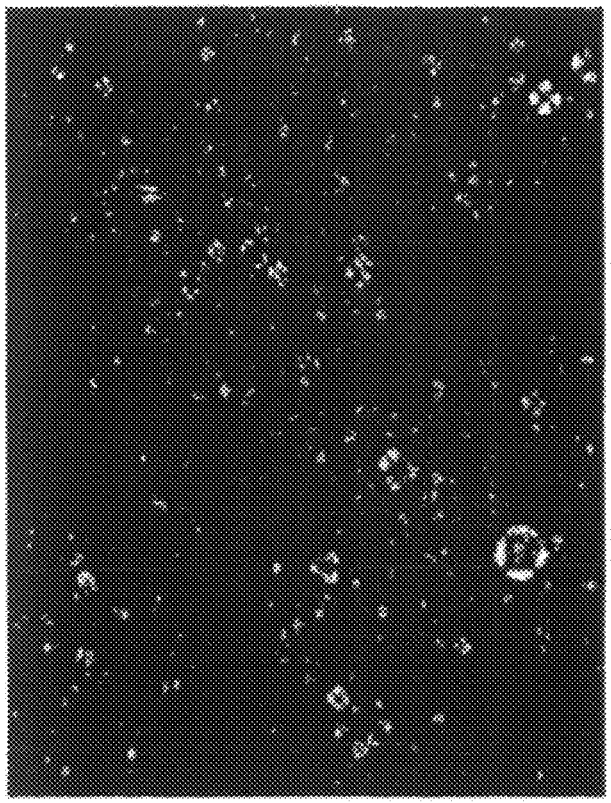
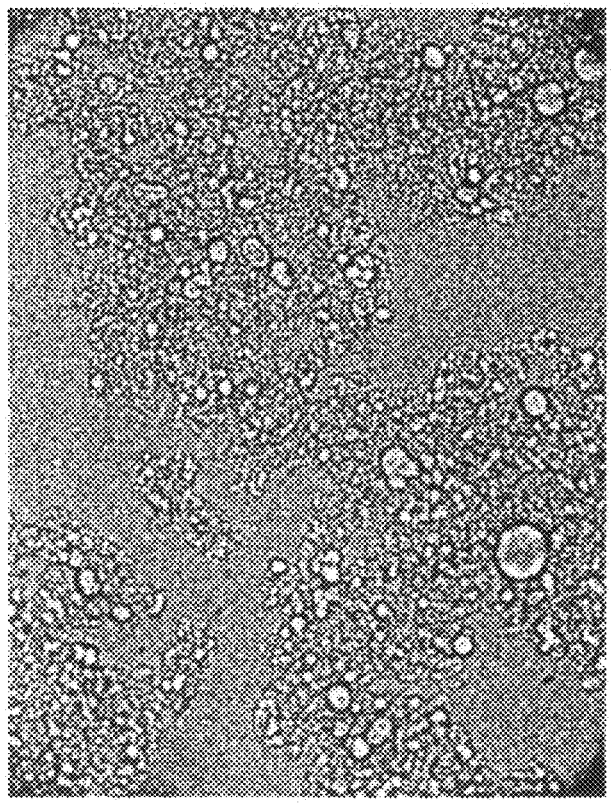

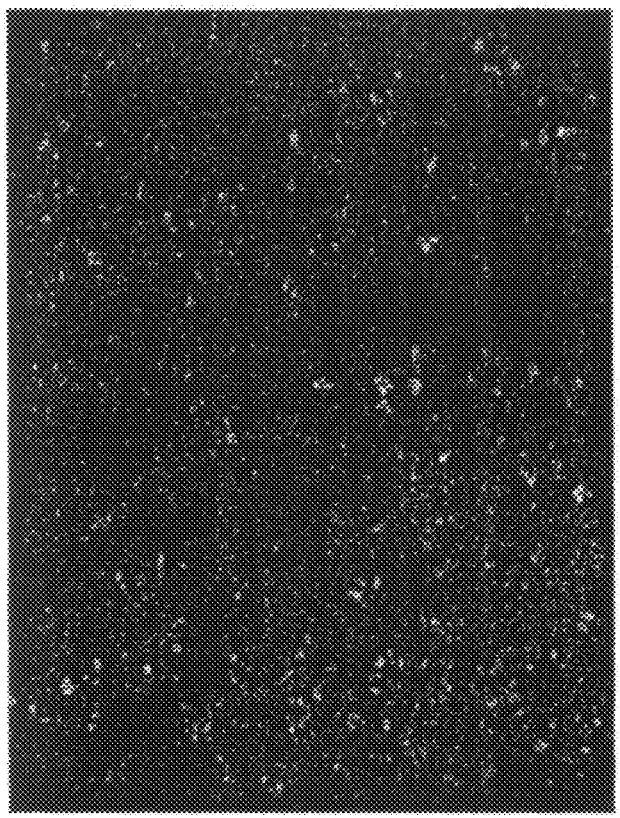
FIG. 6
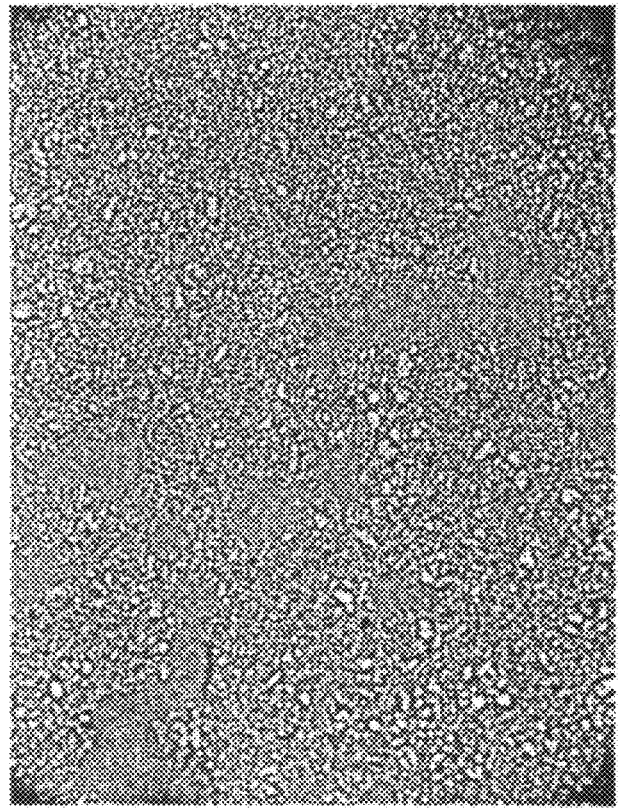

FORMULATION OF INSOLUBLE SMALL MOLECULE THERAPEUTICS IN LIPID-BASED CARRIERS

CROSS REFERENCE TO RELATED APPLICATION

This application claims the benefit under 35 U.S.C. 119(e) of the filing date of U.S. application Ser. No. 60/742,954, filed Dec. 6, 2005, which is incorporated herein by reference.

FIELD

The present invention relates generally to formulations of at least one unsaturated amphiphilic lipid and an amphipathic or hydrophobic drug and methods of making these formulations. More specifically, the present invention relates to formulations of at least one unsaturated phospholipid and an amphipathic or hydrophobic 2,4-pyrimidinediamine drug, methods of making these formulations and the use of such formulations in a variety of contexts, including, for example, the treatment of proliferative disorders, such as tumors and cancers.

BACKGROUND

Many drugs with substantial in vitro biological activity lack therapeutic efficacy in vivo because of poor aqueous solubility. The rate at which a drug dissolves in vivo from a particular dosage form is often the limiting step in determining absorption and often is strongly correlated with the therapeutic efficacy of the drug.

Lipid-based liquid formulations (e.g., liposomes and/or vesicles) have been used to deliver poorly soluble or insoluble small molecule therapeutics with poor bioavailability, particularly anticancer agents (Campbell et al., U.S. Pat. No. 6,680,068; Asvar et al. U.S. Pat. No. 6,689,381, Bernstein et al., U.S. Pat. No. 6,423,345; Knight et al., U.S. Pat. No. 5,049,388; Radhakrishnan et al., U.S. Pat. No. 4,895,719). Typically, in liposomes and/or vesicles the small molecule therapeutic agent is sequestered in an aqueous core surrounded by lipid. Accordingly, such formulations are usually administered intravenously or by inhalation.

Advantages associated with lipid-based formulations include inertness, superior toxicity profiles and safe handling. Lipid-based dispersions where amphipathic or hydrophobic compounds are effectively solubilized in aqueous solution by dissolution in lipid bilayer matrices are potentially very valuable since the drug may potentially be administered orally, intraperitoneally and intranasally as well as intravenously or by inhalation with increased bioavailability. Accordingly, what is needed are lipid-based formulations which facilitate delivery and increase bioavailability, particularly via oral administration of amphipathic or hydrophobic drugs. These novel formulations will typically increase the bioavailability of the amphipathic or hydrophobic drug.

SUMMARY

The present invention satisfies these and other needs by providing novel lipid-based formulations of amphipathic or hydrophobic drugs or pharmaceutically acceptable salts, hydrates, solvates, or N-oxides thereof and methods of making these formulations. In some embodiments, the amphipathic or hydrophobic drug is solubilized by dissolution in lipid bilayer matrices and may be administered orally, intraperitoneally and intranasally, as well as intravenously or by inhalation.

In one aspect, a lipid-based formulation is provided which contains at least one unsaturated amphiphilic lipid and an amphipathic or hydrophobic drug or pharmaceutically acceptable salts, hydrates, solvates or N-oxides thereof. In some embodiments, the unsaturated amphiphilic lipid is a phospholipid and the amphipathic or hydrophobic drug is a pyrimidine derivative, particularly a 2,4-pyrimidinediamine derivative. In other embodiments, the drug and the lipid are present in a ratio ranging from between about 0.015 and about 0.15 on a mole/mole basis.

In another aspect, a method of making a lipid-based formulation is provided. At least one unsaturated amphiphilic lipid, an amphipathic or hydrophobic drug and a solvent are mixed. The solvent is removed to form a residue comprising drug and lipid. The residue is then mixed with water or an aqueous solution. Preferably, the drug and the lipid are present in a ratio ranging from between about 0.015 and about 0.15 on a mole/mole basis.

Many 2,4-pyrimidinediamine derivatives are potent inhibitors of proliferation abnormal cells, such as tumor cell proliferation, in in vitro assays. Thus, in still another aspect, methods of inhibiting proliferation of abnormal cells, in particular tumor cells are provided. The method generally involves contacting an abnormal cell such as a tumor cells with an amount of a formulation containing one or more amphipathic or hydrophobic 2,4-pyrimidinediamine derivatives or prodrugs thereof, or pharmaceutically acceptable salts, hydrates, solvates or N-oxides thereof and an unsaturated amphiphilic lipid effective to inhibit its proliferation. The method may be practiced in in vitro contexts or in in vivo contexts as a therapeutic approach towards the treatment or prevention of proliferative disorders, such as tumorigenic cancers.

In still another aspect, methods of treating proliferative disorders are provided. The methods may be practiced in animals in veterinary contexts or in humans. The methods generally involve administering to an animal or human subject an amount of a formulation containing one or more amphipathic or hydrophobic 2,4-pyrimidinediamine derivatives or prodrugs, or pharmaceutically acceptable salts, hydrates, solvates or N-oxides thereof and an unsaturated amphiphilic lipid, effective to treat the disorder. Proliferative disorders that can be treated according to the methods include, but are not limited to, tumorigenic cancers.

BRIEF DESCRIPTION OF THE DRAWINGS

FIG. 2 shows a polarized light microscopy image of a formulation containing 1,2-dioleoyl-sn-glycero-3-phosphocholine (DOPC) and amphipathic drug 1 in phosphate buffered saline (PBS);

FIG. 3 shows a polarized light microscopy image of a formulation containing DOPC and amphipathic drug 2 in phosphate buffered saline;

FIG. 4 shows a polarized light microscopy image of a formulation containing DOPC and amphipathic drug 3 in phosphate buffered saline;

FIG. 5 shows a polarized light microscopy image of a formulation containing DOPC and amphipathic drug 4 in phosphate buffered saline;

FIG. 6 shows a polarized light microscopy image of a formulation containing DOPC and amphipathic drug 5 in phosphate buffered saline;

DETAILED DESCRIPTION

Definitions

Figure 1:
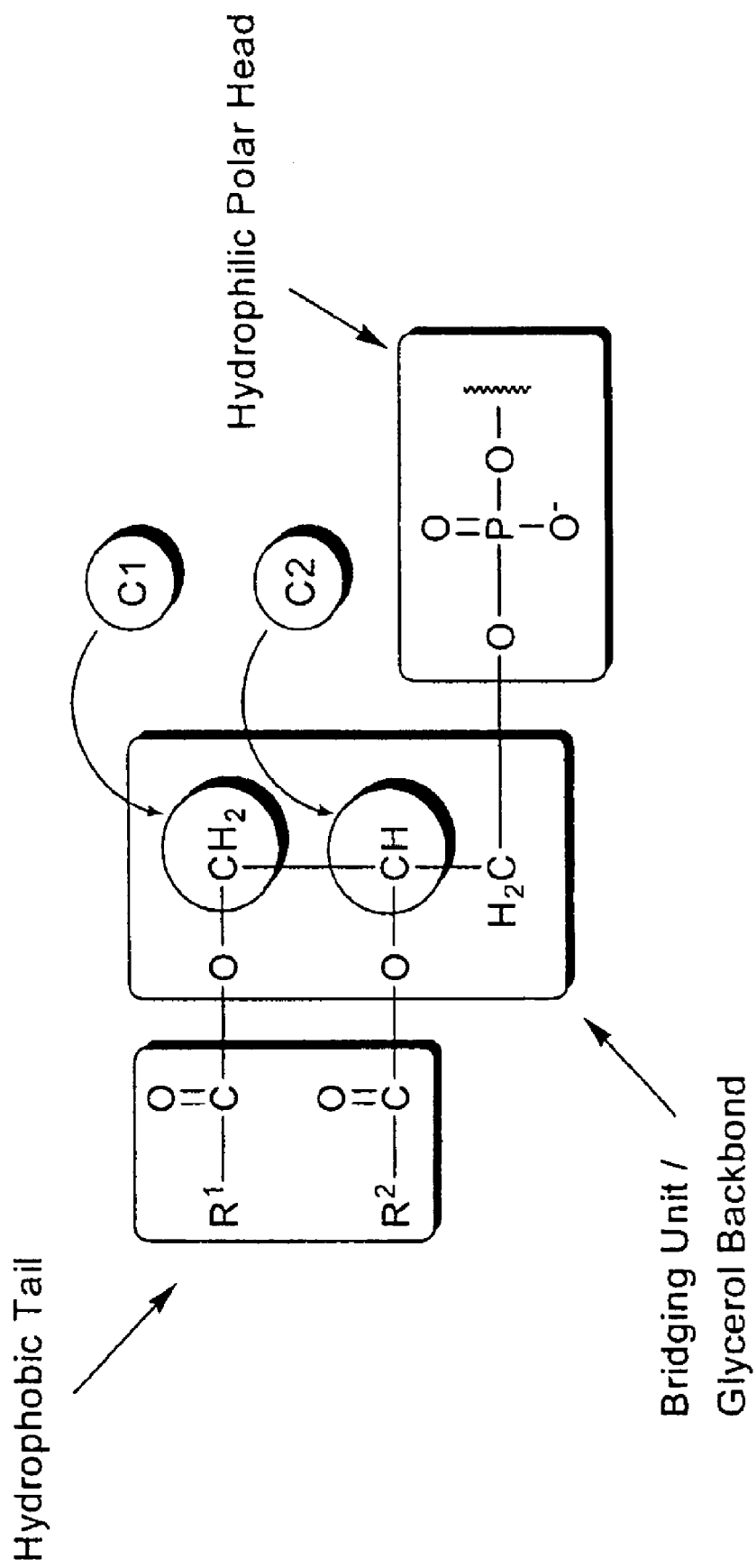
FIG. 1 schematically illustrates one contemplated lipid embodiment of the present invention.

As used herein, the following terms are intended to have the following meanings:

"Alkyl" by itself or as part of another substituent refers to a saturated or branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Pharmaceutically acceptable salt" refers to a salt of a drug which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which an amphipathic or hydrophobic drug is administered.

Formulations

The present invention provides novel lipid-based formulations of amphipathic or hydrophobic drugs. The lipid-based formulations have at least one unsaturated amphiphilic lipid and an amphipathic or hydrophobic drug or pharmaceutically acceptable salts, hydrates, solvates or N-oxides thereof. In some embodiments, the unsaturated amphiphilic lipid is a phospholipid and the amphipathic or hydrophobic drug is a pyrimidine derivative, particularly a 2,4-pyrimidinediamine derivative. In other embodiments, the amphipathic drug is solubilized by dissolution in lipid bilayer matrices and may be administered orally, intraperitoneally and intranasally as well as intravenously or by inhalation. In some other embodiments, the drug and lipid are present in a ratio ranging from between about 0.015 and about 0.15 on a mole/mole basis.

Amphipathic drugs contain both hydrophilic and hydrophobic moieties. Examples of hydrophilic moieties include, but are not limited to, acyl groups, amines, amine salts, hydroxyls, carboxylic acid, carboxylic acid salts, ketones, aldehydes, ethers, thiols, esters, amides and halogens (e.g., fluoro, chloro, bromo, and iodo). Examples of hydrophobic moieties include linear and branched hydrocarbon chains, aromatic groups and other functionality that results in non-polar bonds. Other hydrophilic and hydrophobic moieties are known to those of skill in the chemical arts.

Many therapeutically important compounds including, for example, antipyretic and anti-inflammatory agents, analgesics, antiarthritics, antispasmodics, antidepressants, antipsychotics, tranquilizers, antianxiety drugs, narcotic antagonists, antiparkinsonism agents, cholinergic antagonists, chemotherapeutic agents, immuno-suppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids and vitamins are amphipathic or hydrophobic compounds. Specific examples of amphipathic or hydrophobic drugs include, but are not limited to, lidocaine, doxorubicin, vinorelbine, sodium thiopental, cholesterol, testosterone, alpha tocopherol, phenyl butazone, diphenyl hydramine, pyriamine and desloratidine.

Pyrimidine derivatives, particularly 2,4-pyrimidinediamine derivatives such as those described in U.S. patent application Ser. Nos. 10/355,543 and 10/631,029, filed Jan. 31, 2003 and Jul. 29, 2003, respectively, the disclosures of which are incorporated herein by reference, are another class of therapeutic agents which are amphipathic or hydrophobic compounds. Specific examples of amphipathic 2,4-pyrimidinediamine derivatives include, but are not limited to, the following:

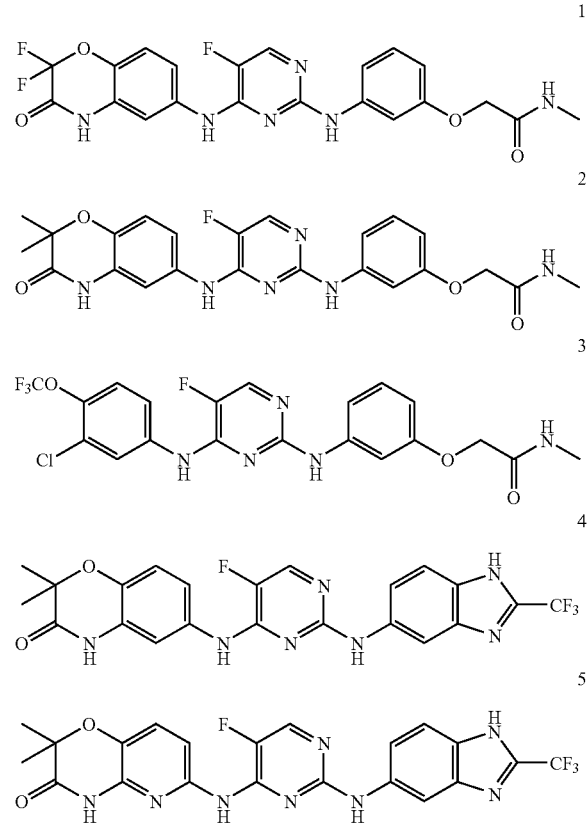

Generally, amphipathic or hydrophobic drugs, have a log P value greater than or equal to about 3 and less than or equal to about 5. The partition coefficient P, is well known to the skilled artisan, and is defined by the formula below:

$$P = C_{n\text{-}octanol}/C_{water}$$

where $C_{n\text{-}octanol}$ is the equilibrium concentration of a lipophilic substance in octanol and $C_{water}$ is the equilibrium concentration of a lipophilic substance in water. Methods for calculating and measuring log P for drug molecules, such as those described, infra, are within the ambit of those of skill in the art.

In general, amphipathic molecules have hydrophilic groups (e.g., chlorine, fluorine, etc.) situated at least one terminal end of the structure. Other amphipathic molecules include compounds with polar chains attached hydrophobic moieties.

Unsaturated amphiphilic lipids contain both hydrophilic groups and hydrophobic regions. Common hydrophilic groups which are found in unsaturated amphiphilic lipids include, but are not limited to, acyl groups, amines, amine salts, hydroxyls, carboxylic acid, carboxylic acid salts, ketones, aldehydes, ethers, thiols, esters, amides, and halogens (e.g., fluoro, chloro, bromo, and iodo). Hydrophobic groups in unsaturated amphiphilic lipids are typically unsaturated hydrocarbon chains of twelve or more carbon atoms.

Examples of broad classes of unsaturated amphiphilic lipids include, for example, detergents, surfactants, soaps, phospholipids, cardiolipids, phosplionolipids (e.g., ceramide phosphonylethylamine), ether lipids, glycoglycerolipids, etc, which are known to those of skill in the art. More specific examples of unsaturated amphiphilic lipids include, but are not limited to, unsaturated fatty acids (e.g., myristoleic, palmitoleic, elaidic, petroseliec, oleic, vaccenic, gondoic, erucic, nervonic, linoleic, gamma-linolenic, alpha linolenic, arachidonic, eicosapentaenoic, docosahexaenoic), the corresponding fatty acid derivatives (e.g., amides, esters, etc.), the corresponding sulfonic acids, the corresponding sulfonic acid derivatives (e.g., sulfonamides, sulfonate esters, etc), the corresponding fatty alcohols, etc.

In some embodiments the lipid includes one or more unsaturated acyl moieties. In other embodiments the amphiphilic lipid is a phospholipid, which includes one or more unsaturated acyl moieties. In some other embodiments, the unsaturated acyl moiety is n-alkenyl. In still other embodiments, the unsaturated acyl moiety is cis-alkenyl. In still other embodiments, the unsaturated acyl moiety is cis-n-alkenyl. In still other embodiments, the unsaturated acyl moiety is $C_{12}$-$C_{24}$ alkenyl. In still other embodiments, the unsaturated acyl moiety is $C_{16}$-$C_{20}$ alkenyl. In still other embodiments, the unsaturated-acyl moiety is selected from the group consisting of petroselinyl, erucyl, oleoyl, elaidoyl, palmitoleoyl, myristoleoyl, arachidonyl, linoleoyl, linolenyl and combinations thereof.

FIG. 1 illustrates an example of a conventional phospholipid, which has a hydrophilic polar head group and a hydrophobic tail interconnected by a bridging unit. In some embodiments, the bridging unit is glycerol and the resulting lipid is a glycerophospholipid. The hydroxyls at C1 and C2 of glycerol may be esterified, for example, with a variety of fatty acids designated as R1 and R2, while the hydroxyl at C3 is esterified with a phosphate moiety to provide a glycerophospholipid. The glycerol backbone, may have either the D-erythro or L-threo configuration.

Examples of unsaturated amphiphilic phospholipids include, but are not limited to phosphatidylcholine, phosphatidylglycerol, phosphatidylserine, phosphatidylethanolamine, phosphatidylinositol, phosphatidic acid, etc. In some embodiments, the unsaturated amphiphilic phospholipid is a phosphatidylcholine. In other embodiments, the unsaturated acyl moiety of the above phospholipids is selected from the group consisting of petroselinyl, erucyl, oleoyl, elaidoyl, palmitoleoyl, myristoleoyl, arachidonyl, linoleoyl, linolenyl and combinations thereof. Examples of phosphatidylcholines include, but are not limited to, dioleoylphosphatidylcholine, dielaidoylphosphatidylcholine, dipetroselinylphosphatidylcholine, dierucylphosphatidylcholine, dipalmitoleoylphosphatidylcholine, dimyristoleoylphosphatidylcholine, diarchidonylphosphatidylcholine, dilinoleoylphosphatidylcholine, dilinolenylphosphatidylcholine, or combination thereof. In some other embodiments, the phosphatidylcholine is dioleoylphosphatidylcholine.

In some embodiments, glycerol substitutes having any combination of nucleophiles (e.g., amines, hydrazines, anilines, azides, hydroxyls, peroxides, thiols, radicals, diradicals or carbon anions) and electrophiles (e.g., carboxylic acid, esters, amides, ketones, aldehydes, epoxides, anhydrides, acid chlorides, alkyl halides, sulfonyl chlorides, sulfonates, sulfinates, isocyanates, isothiocyanates, ketenes, boronates, phosphonates, phosphoryl chlorides or phosphinates) can be used as the backbone for a variety of phospholipids. For example, suitable glycerol substitutes include erythrose, threose, sphingosine, phytosphingosine, sphinganine, etc.

Other unsaturated amphiphilic phospholipids include sphingolipids, such as, for example, sphingosine, phytosphingosine and sphinganine. Sphingosine, phytosphingosine and sphinganine, have an amino functionality that is N-amidated with a fatty acid molecule to provide ceramides. Examples of ceramides include sphingomyelin, ceramide phosphorylinositol, glycosyl ceramides, sulfoglycosphingolipids and oligoglycosyl ceramides (e.g., gangliosides).

Still other unsaturated amphiphilic lipids include unsaturated lipids modified with polyethylene glycol or surfactants containing polyethylene glycol. These pegylated lipids are typically substantially more stable in vivo than their unpegylated counterparts. Such pegylated lipids can be synthesized by conventional methods or are commercially available (Avanti Polar Lipids, Inc., Alabaster, Ala.).

Many unsaturated amphiphilic lipids can be extracted from natural sources (e.g., egg yolk, brain, or plant sources), purchased commercially (e.g., from Sigma-Aldrich and Avanti Polar Lipids) or synthesized by methods known to the skilled artisan (e.g., "Phospholipids Handbook," G. Cevc, ed., Marcel Dekker (1993); Hermanson, "Bioconjugate Techniques" Academic Press (1996); Subramanian et al., *ARKIVOC VII*: 116-125 (2002)).

An important characteristic of unsaturated amphiphilic lipids is the transition temperature ($T_m$) which is typically lower in unsaturated lipids relative to their saturated analogs. Above the transition temperature, a lipid is typically in a liquid crystalline phase characterized by fluid-like properties while below the transition temperature the lipid is usually in a rigid gel phase. Amphipathic or hydrophobic drugs may dissolve in lipids with transition temperatures below physiological temperatures.

TABLE 10

| Fatty Acid | No. Carbons:No. Double Bonds | $T_m$ (° C.) |
| --- | --- | --- |
| Dimyristoylphosphatidylcholine | 14:0 | 23 |
| Dipalmitoylphosphatidylcholine | 16:0 | 41 |
| Distearoylphosphatidylcholine | 18:0 | 55 |
| Dioleoylphosphatidylcholine | 18:1 | −22 |

As shown in Table 10, infra, $T_m$ depends on the length and degree of saturation of the hydrophobic chains in a lipid. Thus, the greater the length and higher the degree of saturation in the hydrophobic chain, the higher the transition temperature for that particular membrane. In some embodiments, the unsaturated amphiphilic lipid has a $T_m$ below about 30° C. In other embodiments, the unsaturated amphiphilic lipid has a $T_m$ below 20° C.

Unsaturated amphiphilic lipids may adopt a number of different structures when placed into an aqueous environment. In some embodiments, the lipid forms a bilayer in an aqueous environment. The lipid bilayer may preferentially sequester an amphipathic or hydrophobic drug from the aqueous environment or alternatively, the amphipathic drug may dissolve in the lipid bilayer.

In other embodiments, the lipid may form a liposome when placed in aqueous solution. Liposomes are self-closed bilayer structures that can self-assemble when amphiphilic lipids are hydrated by water. Typically, liposomes have an aqueous core surrounded by a hydrophobic lipid bilayer. Here, hydrophilic polar groups are directed inward and outward towards aqueous solution and hydrophobic fatty acids associate with one another within the lipid bilayer. In some embodiments, an amphipathic drug or hydrophobic drug is dissolved in the lipid bilayer of the liposome. In other embodiments, the amphipathic drug or hydrophobic drug is in the aqueous core of the liposome.

Liposomes may be small unimellar, large unimellar or multimellar or combinations thereof. Small unilamellar liposomes are about 20 nm to 200 nm in diameter while large unimellar is approximately 1 micron. Multilamellar liposomes typically have concentric bilayers. Oligolamellar liposomes are usually described as multilamellar liposomes with increased aqueous space between bilayers or which have liposomes nested within bilayers in a non-concentric fashion. Multilamellar and oligolamellar liposomes can be conveniently reduced to unilamellar liposomes by mechanical energy (e.g., extrusion) or sonic energy (e.g., sonication). Liposome kits are commercially available (e.g., from Boehringer-Mannheim, ProMega, and Life Technologies (Gibco)).

In some other embodiments, the lipid may form micelles upon exposure to an aqueous environment. Micelles are colloidal aggregates which form when the concentration of amphiphilic lipids reach a critical micelle concentration (CMC). Amphiphilic lipids arrange spontaneously at the critical micelle concentration such that the hydrophilic groups shield the non-polar interior against water in an aqueous environment. Micelles, as is well known in the ail, may be spherical, oblate, prolate or cubic.

In other embodiments, amphiphilic lipids may form microspheres, aggregates, suspensions, colloids, dispersions, emulsions or combinations thereof, either alone or as equilibrium mixtures with micelles, liposomes or lipid bilayers. Accordingly, all such structures and combinations thereof are within the scope of the instant invention.

In some embodiments, the drug is a pyrimidine derivative and the lipid is a phospholipid. Preferably, the pyrimidine derivative is a 2,4-pyrimidinediamine derivative. In other embodiments, the phospholipid is phosphatidylcholine and the 2,4-pyrimidine derivative is one of the compounds illustrated below:

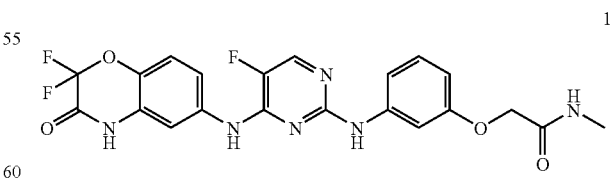

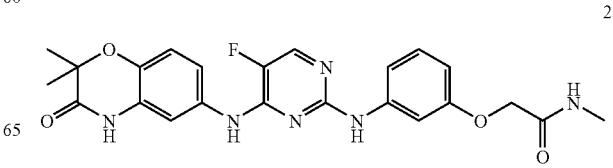

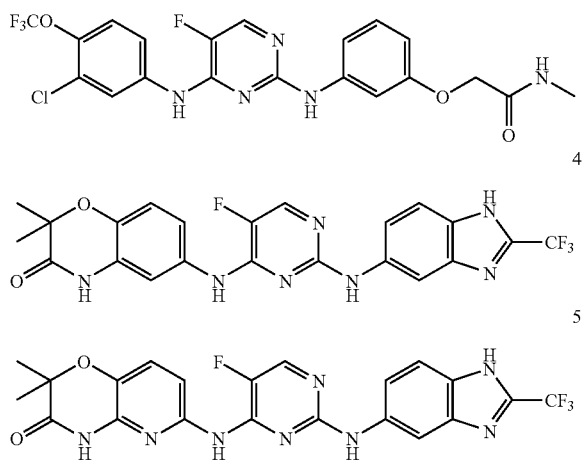

Preferably in the above embodiments, the phosphatidylcholine is dielaidoylphosphatidylcholine, dipetroselinylphosphatidylcholine, dierucylphosphatidylcholine, dipalmitoleoylphosphatidylcholine, dimyristoleoylphosphatidylcholine, diarchidonylphosphatidylcholine, dilinoleoylphosphatidylcholine, dilinolenylphosphatidylcholine, or combinations thereof. In other embodiments, the phosphatidylcholine is dioleoylphosphatidylcholine. In still other embodiments, the pyrimidine is

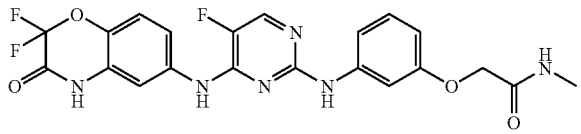

and the phospholipid is dioleoylphosphatidylcholine.

Loading capacity is the amount of amphipathic or hydrophobic drug that saturates an unsaturated amphiphilic lipid. The loading capacity of an amphiphilic lipid is determined by a number of factors including the partition coefficient of the hydrophobic or amphipathic drug as well as the physical and chemical properties of the drug and the hydrophobic properties of lipid. In some embodiments, the lipid has a loading capacity of an amphipathic or hydrophobic drug in a range between about 2 mg/mL and about 8 mg/mL. In other embodiments, the ratio of the amphipathic or hydrophobic drug and unsaturated amphiphilic lipid ranges from between about 0.015 and about 0.15 on a mole/mole basis. In some other embodiments, the ratio of the amphipathic or hydrophobic drug and unsaturated amphiphilic lipid ranges from between about 0.05 and about 0.12 on a mole/mole basis. In still other embodiments, the ratio of the amphipathic or hydrophobic drug and unsaturated amphiphilic lipid is about 0.10 on a mole/mole basis.

Unsaturated amphipathic lipids may be formulated with saturated lipids to vary the transition temperature ($T_m$) and the loading capacity. Saturated lipids include, for example, detergents, surfactants, soaps, phospholipids having two saturated fatty acid chains and phospholipids having a single saturated fatty acid chain, such as lysophatidylcholines. Saturated fatty chains can be selected from the group consisting of butyric, caproic, caprylic, capric, lauric, myristic, palmitic, stearic, arachidic and behenic acids. Detergents include, but are not limited to, α-tocopherol polyethylene glycol succinate (TPGS), PS-80, sodium cholate, sodium dodecylsulfate, sodium salts of N-lauroylsarcosine, lauryldimethylamine-oxide, cetyltrimethylammonium bromide and sodium salt of bis(2-ethylhexyl)sulfosuccinate. Other suitable vehicles are described infra.

Suitable vehicles include, but are not limited to, polyoxyethylene-polyoxypropylene (POE-POP) block copolymers, cyclodextrins (e.g., β-cyclodextrin, γ-cyclodextrin), cyclodextrin derivatives (e.g., sulfobutyl or hydroxypropyl), polyoxyl 40 castor oil, polyoxyl 35 castor oil, PEG-8 caprylic/capric glycerides (Labrasol®), sorbitan monooleate (Span-80), sorbitan monolaurate (Span 20), PEG-20 sorbitan monopalmitate (Tween 40), PEG-20 sorbitan monostearate (Tween 60), PEG-20 sorbitan monooleate (polysorbate 80 or Tween 80), glyceryl mono/dioleate (Capmul GMO-K), glyceryl caprylate/caprate (Capmul MCM), caprylic acid mono/diglycerides (Imwitor® 988), and mono- and diacetylated monoglycerides (Myvacet® 9-45), linoleoyl monoglycerides (Labrafil 2125CS), lauroyl macrogol-32 glycerides (Gelucire® 44/14), α-tocopherol, α-tocopherol acetate, α-tocopherol succinate, α-tocopherol polyethyleneglycol (200-8000 MW) succinate, α-tocopherol polyethylene glycol 400 succinate, dl-α-tocopherol polyethyleneglycol 1000 succinate and d-α-tocopherol polyethyleneglycol 1000 succinate fatty acids, alcohols, fatty acid derivatives, bile acid, sterol, modulator, polymeric materials, solvents, additives, sugars, antioxidants, stabilizers, chelators, emulsifiers, surfactants, detergents, or mixtures thereof.

Fatty acids and alcohols include but are not limited to, $C_6$-$C_{22}$ fatty acids and alcohols, such as stearyl alcohol, capric acid, caprylic acid, lauric acid, myristic acid, stearic acid, oleic acid, linoleic acid, linolenic acid, arachnidoic acid, behenic acid, and their corresponding pharmaceutically acceptable salts. Fatty acid and fatty alcohol derivatives include, but are not limited to, sodium dioctyl sulfosuccinate, sodium lauryl sulfate, amide esters, (e.g., lauric acid diethanolamide, sodium lauryl sarcosinate, lauroyl carnitine, palmitoyl carnitine and myristoyl carnitine), esters with hydroxy-acids (e.g., sodium stearoyl lactylate), sugar esters (e.g., lauryl lactate, glucose monocaprylate, diglucose monocaprylate, sucrose laurate, sorbitan monolaurate (Arlacel® 20), sorbitan monopalmitate (Span-40), sorbitan monooleate (Span-80), sorbitan monostearate and sorbitan tristearate), lower alcohol fatty acid esters (e.g., ethyl oleate (Crodamol EO), isopropyl myristate (Crodamol IPM) and isopropyl palmitate (Crodamol IPP)) esters with propylene glycol (e.g., propylene glycol monolaurate (Lauroglycol FCC), propylene glycol ricinoleate (Propymuls), propylene glycol monooleate (Myverol® P-O6), propylene glycol monocaprylate (Capryol® 90), propylene glycol dicaprylate/dicaprate (Captex® 200) and propylene glycol dioctanoate (Captex 800)), esters with glycerol (e.g., glyceryl monooleate (Peceol), glyceryl ricinoleate, glyceryl laurate, glyceryl dilaurate (Capmul® GDL), glyceryl dioleate (Capmul GDO), glycerol monolinoleate (Maisine®), glyceryl mono/dioleate (Capmul GMO-K), glyceryl caprylate/caprate (Capmul MCM), caprylic acid mono/diglycerides (Imwitor® 988), mono- and diacetylated monoglycerides (Myvacet® 9-45), triglycerides (e.g., corn oil, almond oil, soybean oil, coconut oil, castor oil, hydrogenated castor oil, hydrogenated coconut oil, Pureco 100, Hydrokote AP5, Captex 300, 350, Miglyol 812, Miglyol 818 and Gelucire 33/01)), mixtures of propylene glycol esters and glycerol esters (e.g., mixture of oleic acid esters of propylene glycol and glycerol (Arlacel 186) and polyglycerized fatty acids such as polyglyceryl oleate (Plurol® Oleique), polyglyceryl-2 dioleate (Nikkol DGDO), polyglyceryl-10 trioleate, polyglyceryl-10 laurate (Nikkol Decaglyn 1-L), polyglyceryl-10 oleate (Nikkol Decaglyn 1-0), and polyglyceryl-10 mono, dioleate (Caprol® PEG 860)). Other fatty acid derivatives include, but are not limited to, polyethoxylated fatty acids, (e.g., PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate) PEG-fatty acid diesters (e.g., PEG-20 dilaurate, PEG-20 dioleate, PEG-20 distearate, PEG-32 dilaurate and PEG-32 dioleate) PEG-fatty acid mono- and di-ester mixtures, polyethylene glycol glycerol fatty acid esters (e.g., PEG'ylated glycerol 12-acyloxy-stearate, PEG-20 glyceryl laurate, PEG-30 glyceryl laurate, PEG-40 glyceryl laurate, PEG-20 glyceryl oleate and PEG-30 glyceryl oleate) and alcohol-oil transesterification products (e.g., polyoxyl 40 castor oil (Cremophoro® RH40), polyoxyl 35 castor oil (Cremophor EL or Incrocas 35), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-60 hydrogenated castor oil (Cremophor RH60), PEG-8 caprylic/capric glycerides (Labrasol®), lauroyl macrogol-32 glycerides (Gelucire® 44/14), linoleoyl macrogolglycerides (Labrafil®), stearoyl macrogol-32 glycerides (Gelucire 50/13), and PEG-6 caprylic/capric glycerides (Softigen® 767)).

Bile acid and sterol derivatives include, but are not limited to, cholate, ursodeoxycholate, chenodeoxycholate, taurochenodeoxycholate, tauroursodeoxycholate, glycochenodeoxycholate, glycoursodeoxycholate, sterols and sterol esters or ethers such as PEG-24 cholesterol ether (Solulan® C-24). Tocol derivatives include derivatives of substances with the tocol structure[2-methyl-2-(4,8,12-trimethyltridecyl)chroman-6-ol] or the tocotrienol structure [2-methyl-2-(4,8,12-trimethyltrideca-3,7,11-trienyl)chroman-6-ol]. In particular, the mono-, di-, trimethyl-tocols, commonly known as tocopherols and their organic acid esters such as the acetate, nicotinate, succinate, and polyethylene glycol succinate esters are included. For example, α-tocopherol acetate, α-tocopherol nicotinate, α-tocopherol succinate, α-tocopherol polyethyleneglycol (200-8000 MW) succinate, α-tocopherol polyethylene glycol 400 succinate, d-α-tocopherol polyethyleneglycol 1000 succinate (Vitamin E-TPGS, Eastman Chemical Co.) are included as mixed racemic dl-forms, and the pure d- and l-enantiomers.

Specific examples of polymeric materials include, without limitation, high molecular weight polyethylene glycol, cellulosics, (e.g., ethyl cellulose, methyl cellulose, hydroxypropyl cellulose, hydroxypropyl methyl cellulose (HPMC), hydroxypropyl methyl cellulose phthalate (HPMCP), hydroxypropyl methyl cellulose succinate (HPMCS), cellulose acetate, cellulose nitrate, cellulose acetate butyrate, cellulose acetate trimellitate, carboxymethylethyl cellulose, cellulose acetate phthalate), shellac, polyethylene, polyvinylchloride, polyvinyl acetate, polyvinyl acetate phthalate (PVAP), acrylic polymers, (e.g., polyacrylic acid (Carbomer), neutral polymers of methacrylates, (e.g., Eudragit Nebr.), methacrylate copolymers with trimethylaminoethylmethacrylate as functional group (e.g., Eudragit Rs, RS 100, RL, RL 100), anionic polymers of methacrylic acids and methacrylates (e.g., Eudragit L 100, L 100-55, S 100), polyvinylpyrrolidone copolymers, (e.g., polyvinylpyrrolidone-vinyl acetate copolymers (Kollidon Va. 64, Kollidon SR)), gelactose mannate, high molecular weight polysaccharide gums and resins (e.g., acacia, xanthan gum, tragacanth, shellac, etc.), glycuronan polymers (e.g., alginic acid and pharmaceutically available salts).

The lipid formulations can optionally include one or more additives. Specific, non-limiting examples of additives are described below. Suitable additives include those commonly utilized to facilitate processing steps such as agglomeration, air suspension chilling, air suspension drying, balling, coacervation, comminution, compression, pelletization, cryopelletization, extrusion, granulation, homogenization, inclusion complexation, lyophilization, nanoencapsulation. melting, mixing, molding, pan coating, solvent dehydration, sonication, spheronization, spray chilling, spray congealing, spray drying, or other processes known in the art. The additive can also be pre-coated or encapsulated. Appropriate coatings are well known in the art.

The formulations can optionally include one or more solvents, i.e., additives, to increase the solubility of the active ingredient or other composition components in the carrier, as distinct from compounds that increase aqueous solubility of the drug. Suitable solvents for use in the formulations of the present invention include without limitation, acids (e.g., acetic acid, propionic acid, butyric acid, lactic acid, pyruvic acid, oxalic acid, malic acid, malonic acid, succinic acid, maleic acid, fumaric acid, tartaric acid, citric acid, benzoic acid, cinnamic acid, mandelic acid, salicylic acid, etc.), alcohols and polyols, (e.g., ethanol, isopropanol, butanol, benzyl alcohol, ethylene glycol, propylene glycol, butanediols and isomers thereof, glycerol, pentaerythritol, sorbitol, maniitol, dimethyl isosorbide, polyethylene glycol, polypropylene glycol, polyvinylalcohol, cellulose derivatives, etc.), ethers of polyethylene glycols having an average molecular weight of about 200 to about 6000 (e.g., tetrahydrofurfuryl alcohol PEG ether (glycofurol, available commercially from BASF under the trade name Tetraglycol) or methoxy PEG (Union Carbide)) amides, (e.g., 2-pyrrolidone, 2-piperidone, caprolactam, N-alkylpyrrolidone, N-hydroxyalkylpyrrolidone, N-alkylpiperidone, N-alkylcaprolactam, dimethyl acetamide, polyvinylpyrrolidone etc.), esters (e.g., ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof, etc.) and other solvents known in the art, such as dimethyl acetamide, dimethyl isosorbide (Arlasolve DMI (ICI)), N-methyl pyrrolidones (Pharmasolve (ISP)), monooctanoin and diethylene glycol monoethyl ether (available from Gattefosse under the trade name Transeutol). Mixtures of solvents are also within the scope of the invention. These compounds are readily available from standard commercial sources or may be synthesized using procedures known to those of skill in the art.

The amount of solvent that can be included in the formulations described herein is not particularly limited. Of course, when such formulations are ultimately administered to a patient, the amount of a given solvent is limited to a bioacceptable amount, which is readily determined by one of skill in the art.

Other additives conventionally used in formulations can be included, and these additives are well known in the art. Such additives include, but are not limited to, anti-adherents (antisticking agents, glidants, Dow promoters, lubricants) (e.g., talc, magnesium stearate, fumed silica (Carbosil, Aerosil), micronized silica (Syloid No. FP 244, Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate) anticoagulants (e.g., acetylated monoglycerides), antifoaming agents (e.g., long-chain alcohols and silicone derivatives), antioxidants (e.g., BHT, BHA, gallic acid, propyl gallate, ascorbic acid, ascorbyl palmitate, 4-hydroxymethyl-2,6-di-tert-butyl phenol, tocopherol, etc.), binders (adhesives), i.e., agents that impart cohesive properties to powdered materials through particle-particle bonding, (e.g., matrix binders (dry starch, dry sugars), film binders (PVP, starch paste, celluloses, bentonite, sucrose)), chemical binders (e.g., polymeric cellulose derivatives, such as carboxy methyl cellulose, HPC, HPMC, etc., sugar syrups, corn syrup, water soluble polysaccharides (e.g., acacia, tragacanth, guar, alginates, etc.), gelatin, gelatin hydrolysate, agar, sucrose, dextrose, non-cellulosic binders (e.g., PVP, PEG, vinyl pyrrolidone copolymers, pregelatinized starch, sorbitol, glucose, etc.), bufferants, where the acid is a pharmaceutically acceptable acid, (e.g., hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, etc.) and where the base is a pharmaceutically acceptable base, (e.g., an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a pharmaceutically acceptable salt of acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid, chelating agents (e.g., EDTA and EDTA salts), coagulants (e.g., alginates) colorants or opaquants, (e.g., titanium dioxide, food dyes, lakes, natural vegetable colorants, iron oxides, silicates, sulfates, magnesium hydroxide and aluminum hydroxide), coolants, (e.g. halogenated hydrocarbons (e.g., trichloroethane, trichloroethylene, dichloromethane, fluorotrichloromethane), diethylether and liquid nitrogen) cryoprotectants (e.g., trehelose, phosphates, citric acid, tartaric acid, gelatin, dextran, mannitol, etc.), diluents or fillers, (e.g., lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose disintegrants or super disintegrants (e.g., croscarmellose sodium, starch, starch derivatives, clays, gums, cellulose, cellulose derivatives, alginates, crosslinked polyvinylpyrrolidone, sodium starch glycolate and microcrystalline cellulose), hydrogen bonding agents, (e.g., magnesium oxide), flavorants or desensitizers, (e.g., spray-dried flavors, essential oils and ethyl vanillin), ion-exchange resins (e.g., styrene/divinyl benzene copolymers, and quaternary ammonium compounds), plasticizers (e.g., polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate), preservatives (e.g., ascorbic acid, boric acid, sorbic acid, benzoic acid, and salts thereof, parabens, phenols, benzyl alcohol, and quaternary ammonium compounds), solvents (e.g., alcohols, ketones, esters, chlorinated hydrocarbons and water) sweeteners, including natural sweeteners (e.g., maltose, sucrose, glucose, sorbitol, glycerin and dextrins), and artificial sweeteners (e.g., aspartame, saccharine and saccharine salts) and thickeners (viscosity modifiers, thickening agents), (e.g., sugars, polyvinylpyrrolidone, cellulosics, polymers and alginates).

Additives can also be materials such as proteins (e.g., collagen, gelatin, Zein, gluten, mussel protein, lipoprotein), carbohydrates (e.g., alginates, carrageenan, cellulose derivatives, pectin, starch, chitosan), gums (e.g., xanthan gum, gum arabic), spermaceti, natural or synthetic waxes, carnuaba wax, fatty acids (e.g., stearic acid, hydroxystearic acid), fatty alcohols, sugars, shellacs, such as those based on sugars (e.g., lactose, sucrose, dextrose) or starches, polysaccharide-based shellacs (e.g., maltodextrin and maltodextrin derivatives, dextrates, cyclodextrin and cyclodextrin derivatives), cellulosic-based shellacs (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate, trimellitate, carboxymethylethyl cellulose, hydroxypropylmethyl cellulose phthalate), inorganics, (e.g., dicalcium phosphate, hydroxyapatite, tricalcium phosphate, talc and titania), polyols (e.g., mannitol, xylitol and sorbitol polyethylene glycol esters) and polymers (e.g., alginates, poly(lactide coglycolide), gelatin, crosslinked gelatin and agar-agar).

Drugs and lipids described herein may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Drugs and lipids described herein may also exist in several tautomeric forms including the enol form, the keto form and mixtures thereof. Accordingly, the chemical structures depicted herein encompass all possible tautomeric forms of the illustrated compounds.

Drugs and lipids described herein also include isotopically labeled compounds where one or more atoms have an atomic mass different from the atomic mass conventionally found in nature. Examples of isotopes that may be incorporated into the compounds include, but are not limited to, $^2H$, $^3H$, $^{11}C$, $^{13}C$, $^{14}C$, $^{15}N$, $^{17}O$ and $^{18}O$.

Drugs and lipids disclosed herein may exist in unsolvated forms as well as solvated forms, including hydrated forms and as N-oxides. In general, the hydrated, solvated and N-oxide forms are within the scope of the present invention. Certain drugs may exist in multiple crystalline or amorphous forms. In general, all physical forms are equivalent for the uses contemplated herein and are intended to be within the scope of the present disclosure.

Methods Of Making Lipid-Based Formulations

The current invention also provides methods for making lipid-based formulations. An amphipathic or hydrophobic drug or pharmaceutically acceptable salts, hydrates, solvates, or N-oxides thereof, at least one unsaturated amphiphilic lipid and a solvent are mixed together and the solvent is then removed to provide a residue of drug and lipid. The residue is then mixed with water or an aqueous solution to provide the lipid-based formulation. In some embodiments, the drug and the lipid are present in a ratio ranging from between about 0.015 and about 0.15 on a mole/mole basis.

The solvent may be an organic solvent, a detergent, a surfactant, or combinations thereof. Organic solvents include, but are not limited to, dichloromethane, chloroform, haloalkanes, ethers, tetrahydrofuran, acetonitrile, dimethyl sulfoxide, dimethyl formamide, alcohols, polyols, water and mixtures thereof. In some embodiments, the organic solvent is dichloromethane.

Detergents include, but are not limited to, TPGS, PS 80, sodium cholate, sodium dodecylsulfate, sodium salt of N-lauroylsarcosine, lauryldimethylamine-oxide, cetyltrimethylammoniumlbromide, the sodium salt of bis(2-ethylhexyl) sulfosuccinate and mixtures thereof. Other detergents have been described, infra.

The mixture can be mixed by a variety of methods including, but not limited to, stirring, spinning, blending, heating, shaking, agitating, sonicating, vortexing, centrifugating, or combination thereof to form a homogenous solution of drug, lipid and solvent. The solvent may be removed by a number of conventional methods including reverse phase evaporation, rotary evaporation, distillation, vacuum evaporation, lyophilization, or inert gas transfer, etc. to provide a residue of drug and lipid. The drug and lipid reside may take any number of physical forms including, but not limited to, a film, oil, liquid, emulsion, suspension, colloid, dispersion, aggregate, microsphere, or combinations thereof. In some embodiments, the residue is a film which may be thoroughly freed of any residual organic solvent by vacuum evaporation.

Hydration of the residue may be accomplished mixing the residue with water or an aqueous solution (e.g., a buffer, saline and non-electrolytes such as sugar solutions). In some embodiments, a phosphate buffer solution is used to hydrate the residue. To ensure thorough mixing, the hydration step can proceed concomitantly or separately with stirring, spinning, blending, heating, shaking, agitating, sonicating, vortexing, centrifugating, etc. In some embodiments, the temperature of the hydrating solution may be heated above the transition temperature of the unsaturated amphiphilic lipid.

Generally, the residue is mixed for at least one hour with the hydrating medium to ensure complete hydration. As will be obvious to the skilled artisan different combinations of drug and lipid will have different hydration times. In some embodiments, the hydrated reside is allowed to stand overnight.

In other embodiments, the consistency and/or viscosity of the reconstituted lipid-drug residue can be adjusted with the addition of salts (e.g., $MgCl_2$, NaCl, KCl, etc.) to the hydrating medium.

Methods Of Using 2,4-Pyrimidinediamine Compounds

The formulations of 2,4-pyrimidinediamines, including the various salts, prodrugs, hydrates and N-oxide forms thereof, may be used to inhibit cell proliferation in a variety of contexts. According to some embodiments of the method, a cell or population of cells is contacted with an amount of such a formulation effective to inhibit proliferation of the cell or cell population. The formulation may act cytotoxically to kill the cell, or cytostatically to inhibit proliferation without killing the cell.

In some embodiments, the methods may be practiced as a therapeutic approach towards the treatment of proliferative disorders. Thus, in a specific embodiment, the formulations of 2,4-pyrimidinediamines (and the various forms described herein) may be used to treat proliferative disorders in animal subjects, including humans. The method generally comprises administering to the subject an amount of a formulation effective to treat the disorder. In one embodiment, the subject is a mammal, including, but not limited to, bovine, horse, feline, canine, rodent, or primate. In another embodiment, the subject is a human.

A variety of cellular proliferative disorders may be treated with the formulations of the present invention. In one embodiment, the formulations are used to treat various cancers in afflicted subjects. Cancers are traditionally classified based on the tissue and cell type from which the cancer cells originate. Carcinomas are considered cancers arising from epithelial cells while sarcomas are considered cancers arising from connective tissues or muscle. Other cancer types include leukemias, which arise from hematopoietic cells, and cancers of nervous system cells, which arise from neural tissue. For non-invasive tumors, adenomas are considered benign epithelial tumors with glandular organization while chondomas are benign tumor arising from cartilage. In the present invention, the described formulations may be used to treat proliferative disorders encompassed by carcinomas, sarcomas, leukemias, neural cell tumors, and non-invasive tumors.

In a specific embodiment, the formulations are used to treat solid tumors arising from various tissue types, including, but not limited to, cancers of the bone, breast, respiratory tract, brain, reproductive organs, digestive tract, urinary tract, eye, liver, skin, head, neck, thyroid, parathyroid, and mestastatic forms thereof.

Specific proliferative disorders include the following: a) proliferative disorders of the breast include, but are not limited to, invasive ductal carcinoma, invasive lobular carcinoma, ductal carcinoma, lobular carcinoma in situ, and metastatic breast cancer; b) proliferative disorders of the skin include, but are not limited to, basal cell carcinoma, squamous cell carcinoma, malignant melanoma, and Karposi's sarcoma; c) proliferative disorders of the respiratory tract include, but are not limited to, small cell and non-small cell lung carcinoma, bronchial adema, pleuropulmonary blastoma, and malignant mesothelioma; d) proliferative disorders of the brain include, but are not limited to, brain stem and hypothalamic glioma, cerebellar and cerebral astrocytoma, medullablastoma, ependymal tumors, oligodendroglial, meningiomas, and neuroectodermal and pineal tumors; e) proliferative disorders of the male reproductive organs include, but are not limited to, prostate cancer, testicular cancer, and penile cancer f) proliferative disorders of the female reproductive organs include, but are not limited to, uterine cancer (endometrial), cervical, ovarian, vaginal, vulval cancers, uterine sarcoma, ovarian germ cell tumor; g) proliferative disorders of the digestive tract include, but are not limited to, anal, colon, colorectal, esophageal, gallbladder, stomach (gastric), pancreatic cancer, pancreatic cancer-Islet cell, rectal, small-intestine, and salivary gland cancers; h) proliferative disorders of the liver include, but are not limited to, hepatocellular carcinoma, cholangiocarcinoma, mixed hepatocellular cholangiocarcinoma, and primary liver cancer; i) proliferative disorders of the eye include, but are not limited to, intraocular melanoma, retinoblastoma, and rhabdomyosarcoma; j) proliferative disorders of the head and cancers include, but are not limited to, laryngeal, hypopharyngeal, nasopharyngeal, oropharyngeal cancers, and lip and oral cancer, squamous neck cancer, metastatic paranasal sinus cancer; k) proliferative disorders of the lymphomas include, but are not limited to, various T cell and B cell lymphomas, non-Hodgkins lymphoma, cutaneous T cell lymphoma, Hodgkins disease, and lymphoma of the central nervous system; 1) leukemias include, but are not limited to, acute myeloid leukemia, acute lymphoblastic leukemia, chronic lymphocytic leukemia, chronic myelogenous leukemia, and hair cell leukemia, m) proliferative disorders of the thyroid include thyroid cancer, thymoma, and malignant thymoma; n) sarcomas include, but are not limited to, sarcoma of the soft tissue, osteosarcoma, malignant fibrous histiocytoma, lymphosarcoma, and rhabdomyosarcoma.

It is to be understood that the descriptions of proliferative disorders is not limited to the conditions described above, but encompasses other disorders characterized by uncontrolled growth and malignancy. It is further understood that proliferative disorders include various metastatic forms of the tumor and cancer types described herein. The 2,4-pyrimidinediamine formulations may be tested for effectiveness against the disorders described herein, and a therapeutically effective regimen established. Effectiveness, as further described below, includes reduction or remission of the tumor, decreases in the rate of cell proliferation, or cytostatic or cytotoxic effect on cell growth.

Combination Therapies

The 2,4-pyrimidinediamine formulations of the present invention may be used alone, in combination with one another, or as an adjunct to, or in conjunction with, other established antiproliferative therapies. Thus, the 2,4-pyrimidinediamine formulations of the present invention may be used with traditional cancer therapies, such as ionization radiation in the form of 7-rays and x-rays, delivered externally or internally by implantation of radioactive compounds, and as a follow-up to surgical removal of tumors.

In another aspect, the 2,4-pyrimidinediamine formulations of the present invention may be used with other chemotherapeutic agents useful for the disorder or condition being treated. These 2,4-pyrimidinediamine formulations may be administered simultaneously, sequentially, by the same route of administration, or by a different route.

In one embodiment, the present 2,4-pyrimidinediamine formulations may be used with other anti-cancer or cytotoxic agents. Various classes of anti-cancer and anti-neoplastic compounds include, but are not limited to, alkylating agents, antimetabolites, vinca alkyloids, taxanes, antibiotics, enzymes, cytokines, platinum coordination complexes, substituted ureas, tyrosine kinase inhibitors, hormones and hormone antagonists. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as anti-neoplastic agents include L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesteron caproate, medroxyprogesterone; and anti-estrogen compound tarnoxifen.

These and other useful anti-cancer compounds are described in *Merck Index,* 13th Ed. (O'Neil M. J. et al., ed) Merck Publishing Group (2001) and *Goodman and Gilmans The Pharmacological Basis of Therapeutics,* 10th Edition, Hardman, J. G. and Limbird, L. E. eds., pg. 1381-1287, McGraw Hill, (1996), both of which are incorporated by reference herein.

Additional anti-proliferative compounds useful in combination with the 2,4-pyrimidinediamine formulations of the present invention include, by way of example and not limitation, antibodies directed against growth factor receptors (e.g., anti-Her2); antibodies for activating T cells (e.g., anti-CTLA-4 antibodies); and cytokines such as interferon-α and interferon-γ, interleukin-2 and GM-CSF.

When used to treat or prevent such diseases, the formulations may be administered singly, as mixtures of one or more formulations or in mixture or combination with other agents useful for treating such diseases and/or the symptoms associated with such diseases. The active compounds may also be administered in mixture or in combination with agents useful to treat other disorders or maladies, such as steroids, membrane stabilizers, etc.

Methods Of Administration

The lipid formulations of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the formulation may take the form of a solution, gel, ointment, creams, suspension, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The formulations for injection may be presented in unit dosage form, e.g., in ampoules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active formulation may be dried by any art-known technique, such as lyophilization, and reconstituted prior to use.

For transmucosal administration, penetrants appropriate to the barrier to be permeated are used in the formulation of the invention. Such penetrants are known in the art.

For oral administration, the formulation may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

For buccal administration, the formulations may take the form of tablets or lozenges formulated in conventional manner.

For rectal and vaginal routes of administration, the formulation may be a solution (for retention enemas), a suppository or an ointment containing conventional suppository bases such as cocoa butter or other glycerides.

For nasal administration or administration by inhalation or insufflation, the formulation can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may contain a powder mix of the formulation and a suitable powder base such as lactose or starch.

For ocular administration, the formulation may be a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the formulation may take the form of a depot preparation for administration by implantation or intramuscular injection. The formulation may contain a suitable polymeric or hydrophobic materials (e.g., as an emulsion in an acceptable oil) or ion exchange resins, or as sparingly soluble derivatives, e.g., as a sparingly soluble salt.

The formulations may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

The formulations will generally be used in an amount effective to achieve the intended result, for example in an amount effective to treat or prevent the particular disease being treated. The formulations may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

Effective Dosages

The amount of formulation administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingi & Woodbury, "General Principles," In: *Goodman and Gilman's The Pharmaceutical Basis of Therapeutics*, Chapter 1, pp. 1-46, latest edition, Pergamon Press, and the references cited therein.

Initial dosages may also be estimated from in vivo data, such as animal models. Animal models useful for testing the efficacy of compounds to treat or prevent the various diseases described above are well-known in the art. Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the formulations may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Kits

The formulations described herein may be assembled in the form of kits. In some embodiments, the kit provides a formulation for administration. The formulation may be in a dry or lyophilized form, or in a solution, particularly a sterile solution. When the formulation is in a dry form, the kit may contain a pharmaceutically acceptable diluent for preparing a liquid formulation. The kit may contain a device for administration or for dispensing the formulation, including, but not limited to syringe, pipette, transdermal patch, or inhalant.

The kits may include other therapeutic compounds for use in conjunction with the formulations described herein. In some embodiments, the therapeutic agents are other anti-cancer and anti-neoplastic compounds. These compounds may be provided in a separate form, or mixed with the formulations of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

EXAMPLES

The invention is further defined by reference to the following examples, which describe lipid formulations and methods for preparing the lipid formulations. It will be apparent to the skilled artisan that many modifications, both of the material and methods may be practiced without depart from the scope of the invention.

Example 1

Preparation of a Lipid Formulation of 1

Compound 1 (7.21 mg, 14.22 mg or 28.17 mg, respectively) and DOPC (356.51 mg, 351.33 mg or 354.20, respectively) were mixed in dichloromethane (1.5 mL). After the lipid and drug were completely dissolved, the solvent was removed by nitrogen gas transfer and the residue was subsequently dried overnight under vacuum to yield a homogeneous film of 1. The film was hydrated with PBS at pH 7.4 (3.15 mL) and vortexed to give a lipid formulation of 1 (compound:lipid mole-to-mole ratio of 0.0331, 0.0663, or 0.1333). The lipid formulation was characterized by polarizing light microscopy (Olympus BX51) (FIG. 1), and differential scanning calorimetry (TA Instruments, Model Q100, New Castle, Del., at heating rate of 10° C./minute with $N_2$ gas flow rate of 50 mL/minute) (FIGS. 7A, 7B, 8 and 9). No crystals were visible in the polarizing light microscopy image indicating complete solubilization of the compound in the lipid formulation.

Figure 7:
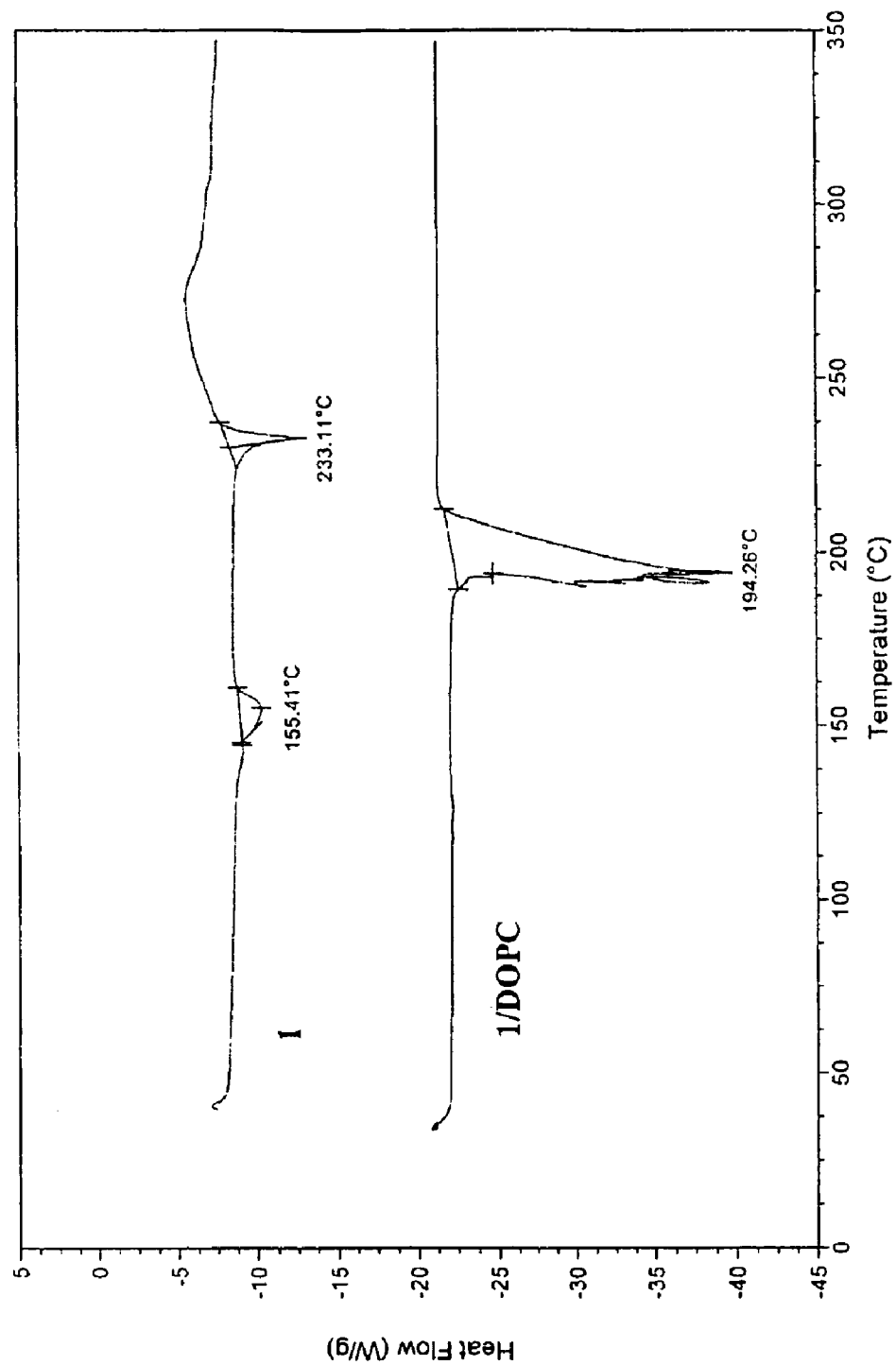
FIG. 7 shows a Differential Scanning Calorimeter (DSC) scan of amphipathic drug 1 (top) in a formulation of DOPC and a DSC amphipathic drug 1 in PBS (bottom)

The DSC scan of 1 in a formulation including DOPC is shown in FIG. 7 (bottom) while the DSC scan of 1 alone is shown in FIG. 7 (top). As illustrated in FIG. 7 the two DSC scans are quite different.

Figure 8:
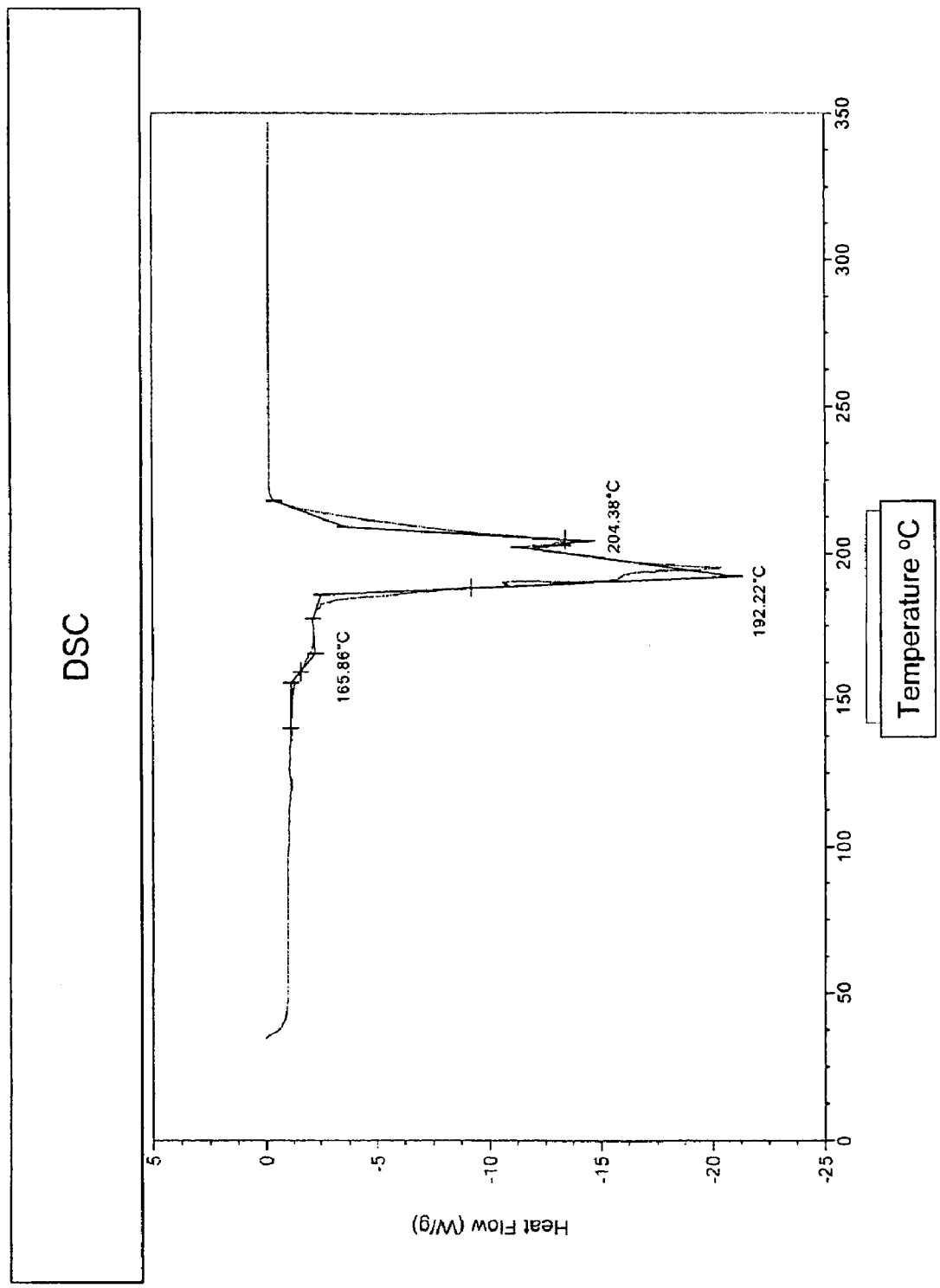
FIG. 8 shows a DSC scan of amphipathic drug 1 in PBS.
Figure 9:
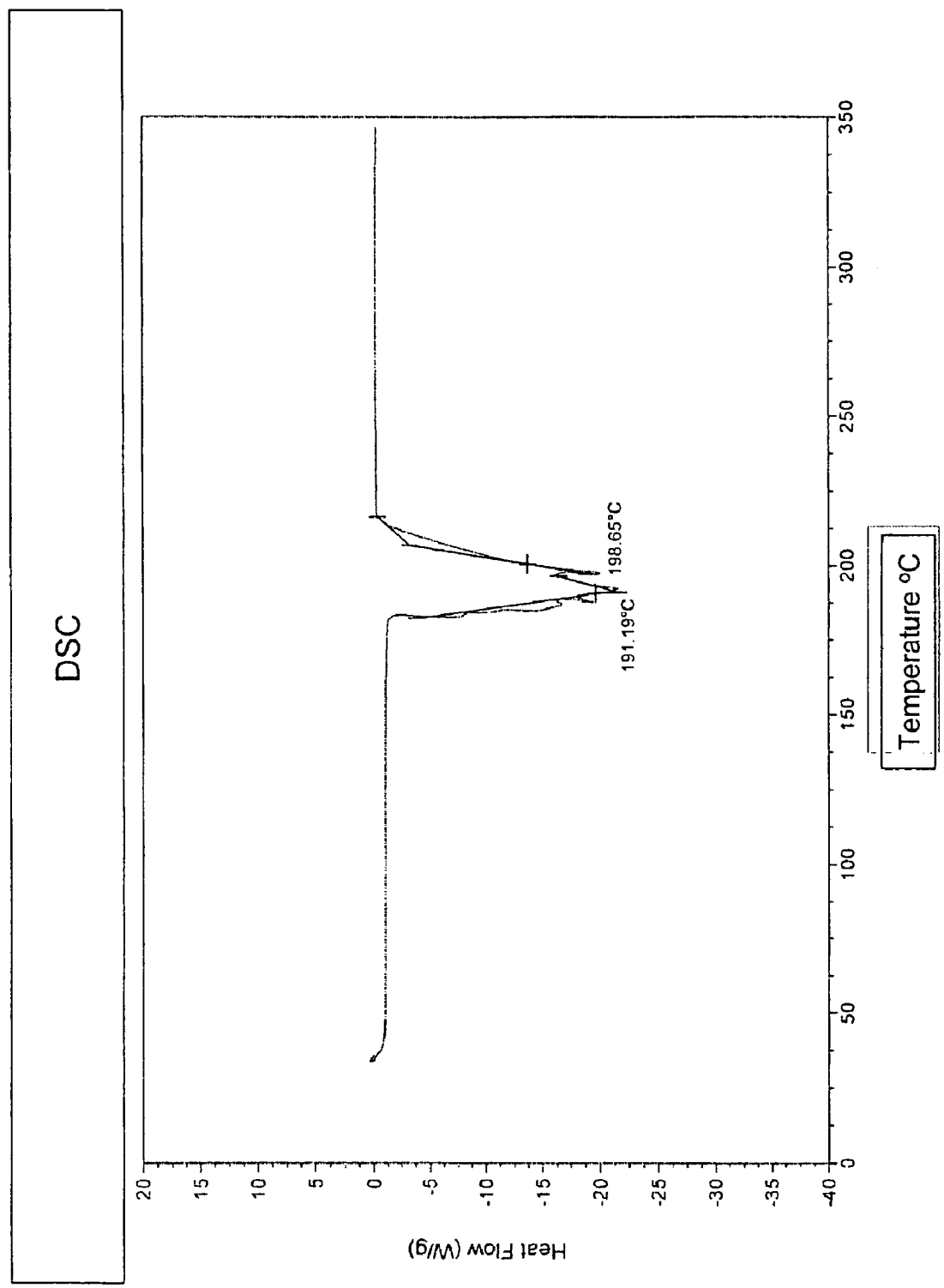
FIG. 9 shows a DSC scan of PBS.

A DSC scan of 1 suspended in a PBS is shown in FIG. 8 and a DSC scan of PBS, alone is shown in FIG. 9.

Example 2

Preparation of Lipid Formulation of 2

Compound 2 (4.27 mg) and DOPC (103.90 mg) were mixed in dichloromethane (1.0 mL), warmed briefly to 40° C. and mixed thoroughly until the compound and DOPC were completely dissolved. The solvent was removed by nitrogen gas transfer and the resulting residue was dried overnight under a vacuum to yield a homogeneous film. The film was then hydrated with PBS at pH 7.4 (0.9 mL) and vortexed to form the lipid formulation (compound:lipid mole-to-mole ratio of 0.0647). The lipid formulation was characterized by polarizing light microscopy (Olympus BX51) (FIG. 2). No crystals were visible in the polarizing light microscopy image indicating complete solubilization of the compound in the lipid formulation.

Example 3

Preparation of Lipid Formulation of 3

Compound 3 (4.25 mg) and DOPC (100.74 mg) were mixed in dichloromethane (1.0 mL), warmed briefly to 40° C. and mixed thoroughly until the compound and DOPC were completely dissolved. The solvent was removed by nitrogen gas transfer and the resulting residue was dried overnight under a vacuum to yield a homogeneous film. The film was then hydrated with PBS at pH 7.4 (0.9 mL) and vortexed to form the lipid formulation (compound:lipid mole-to-mole ratio of 0.0647). The lipid formulation was characterized by polarizing light microscopy (Olympus BX51) (FIG. 3). No crystals were visible in the polarizing light microscopy image indicating complete solubilization of the compound in the lipid formulation.

Example 4

Preparation of Lipid Formulation of 4

Compound 4 (1.97 mg) and DOPC (51.8 mg) were mixed in dichloromethane (1.0 mL), warmed briefly to 40° C. and mixed thoroughly until the compound and DOPC were completely dissolved. The solvent was removed by nitrogen gas transfer and the resulting residue was dried overnight under a vacuum to yield a homogeneous film. The film was then hydrated with PBS at pH 7.4 (0.45 mL) and vortexed to form the lipid formulation (compound:lipid mole-to-mole ratio of 0.0645). The lipid formulation was characterized by polarizing light microscopy (Olympus BX51) (FIG. 4). No crystals were visible in the polarizing light microscopy image indicating complete solubilization of the compound in the lipid formulation.

Example 5

Preparation of Lipid Formulation of 5

Compound 5 (1.97 mg) and DOPC (51.8 mg) were mixed in dichloromethane (1.0 mL), warmed briefly to 37° C. and mixed thoroughly until the compound and DOPC were completely dissolved. The solvent was removed by nitrogen gas transfer and the resulting residue was dried overnight under a vacuum to yield a homogeneous film. The film was then hydrated with PBS at pH 7.4 (0.45 mL) and vortexed to form the lipid formulation (compound:lipid mole-to-mole ratio of 0.0644). The lipid formulation was characterized by polarizing light microscopy (Olympus BX51) (FIG. 3). No crystals were visible in the polarizing light microscopy image indicating complete solubilization of the compound in the lipid formulation.

Example 6

Mouse Pharmacokinetic Studies of Lipid Formulation of 1

Figure 10B:
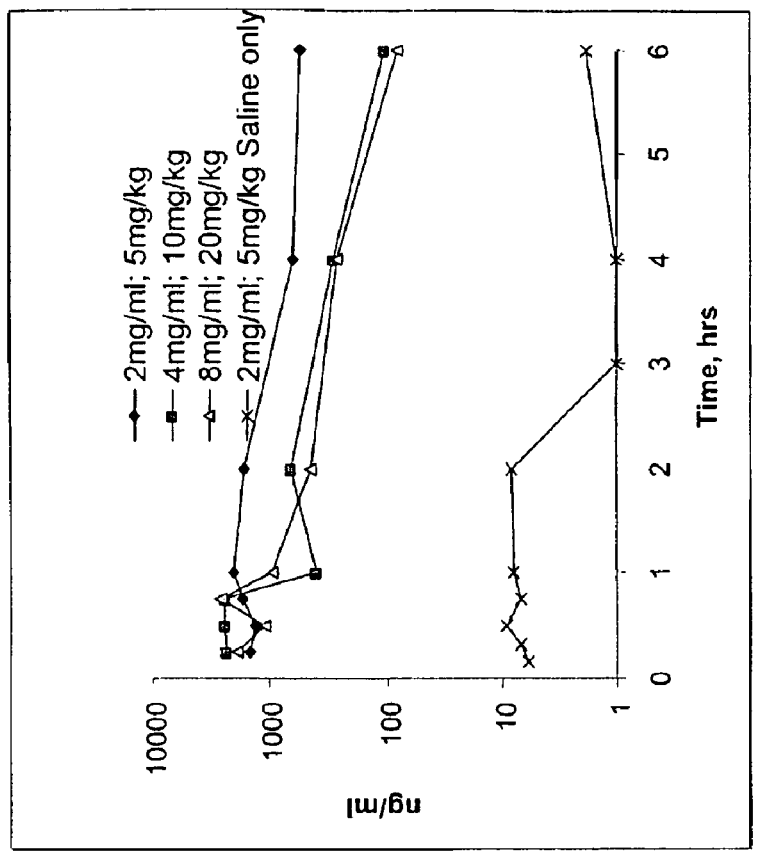
FIG. 10B is a plot illustrating the normalized results of the mouse pharmacokinetics study in FIG. 10A.
Figure 10A:
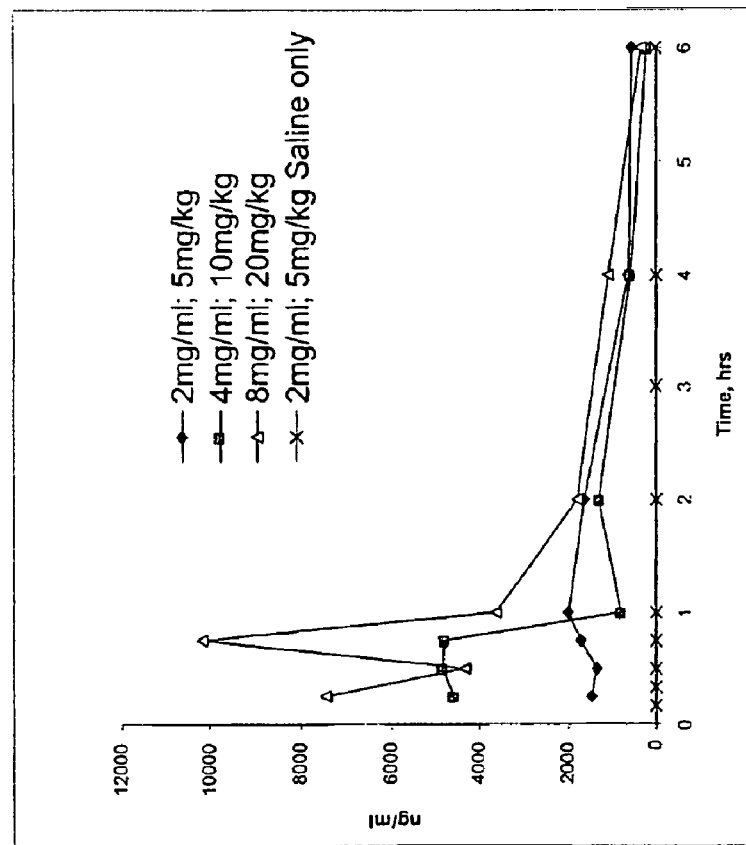
FIG. 10A illustrates a mouse pharmacokinetics study measuring the concentration of amphipathic drug 1 with respect to time. A formulation of 1 and DOPC in PBS was administered intraperitoneally to Balb/C mice.

Mouse pharmacokinetic studies were conducted with Balb/C mice. The lipid formulation of 1 was administered intraperitoneally to measure the concentration of 1 in mice over time. The results of the pharmacokinetic studies are shown in FIGS. 10A and 10B. As demonstrated in FIG. 10A, the pharmacokinetic studies indicate that the lipid formulation of 1 enhances the $C_{max}$ of 1 by 20 folds relative to the administration of 1 intraperitoneally as a saline suspension without a lipid vehicle.

Normalization of FIG. 10A, with respect to the kinetic results for 1 (2 mg/mL, 5 mg/kg) suspended in saline without a lipid vehicle, is shown in FIG. 10B. FIG. 10B emphasizes the increase in $C_{max}$ is FIG. 10A is due to the solubilization of 1 in the lipid vehicle.

Example 7

Rat Pharmacokinetic Studies of the Lipid Formulation of 1

Figure 11:
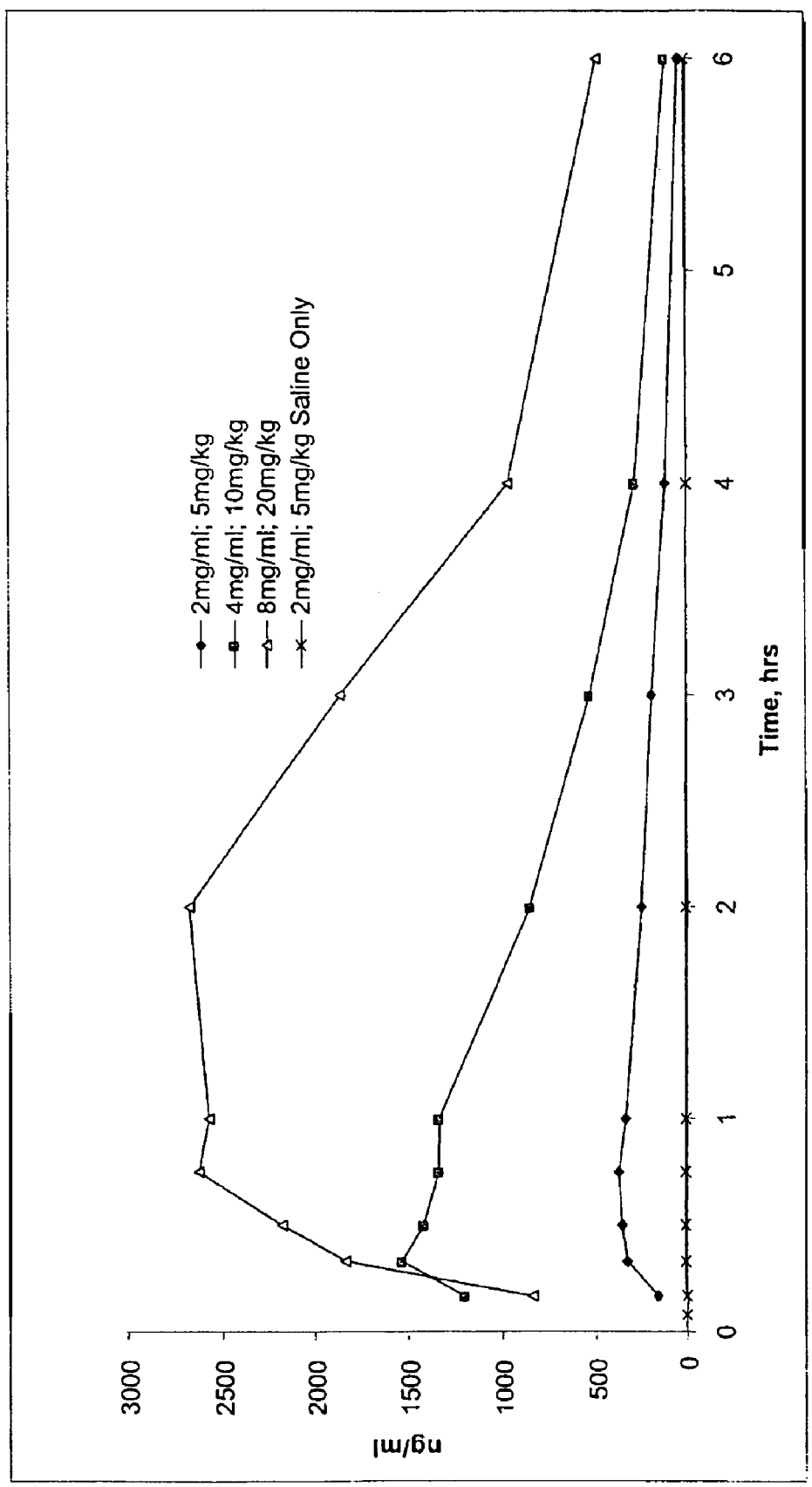
FIG. 11 is a plot illustrating a rat pharmacokinetics study measuring the concentration of amphipathic drug 1 with respect to time. A formulation of 1 and DOPC in PBS was administered intraperitoneally to Sprague-Dawley rats.

Rat pharmacokinetic studies were conducted with Sprague Dawley rats. The lipid formulation of 1 was administered intraperitoneally to measure the concentration of 1 in rats over time. The results of the pharmacokinetic studies are shown in FIG. 11. As shown in FIG. 11, the pharmacokinetic studies [normalized against 1 (2 mg/mL; 5 mg/kg) suspended in saline without a lipid vehicle] indicate that a formulation having a lipid vehicle to solubilize 1 greatly increases the $C_{max}$ of 1 in rats.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the claim(s) issuing herefrom. All publications and patents cited herein are incorporated by reference in their entirety.

What is claimed is:

1. A liposomal formulation comprising at least one unsaturated amphiphilic lipid and a 2,4-pyrimidinediamine drug selected from

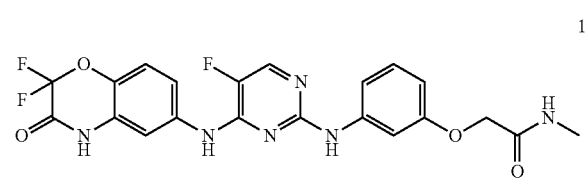

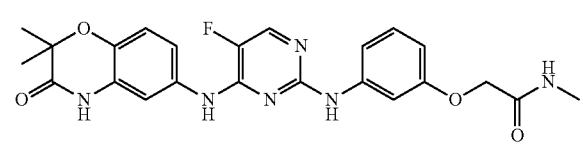

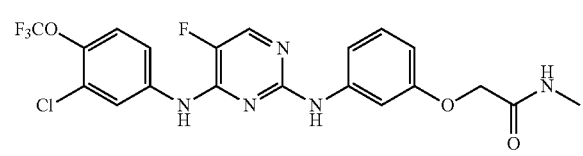

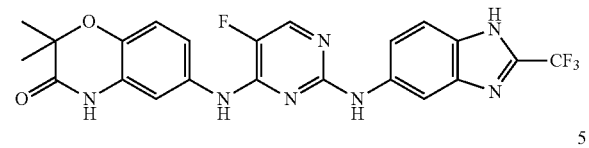

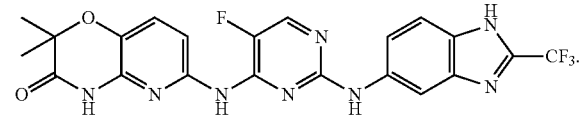

or pharmaceutically acceptable salts, hydrates, or solvates thereof, wherein the drug and the lipid are present in a ratio ranging from between about 0.015 and about 0.15 on a mole/mole basis.

2. The formulation of claim 1 further comprising a pharmaceutically acceptable vehicle.

3. The formulation of claim 1 in which the 2,4-pyrimidinediamine is

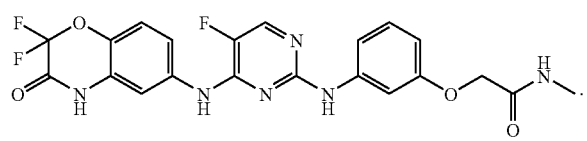

4. The formulation of claim 1 in which the lipid has a transition temperature below about 30° C.

5. The formulation of claim 1 in which the lipid includes one or more unsaturated acyl moieties.

6. The formulation of claim 1 in which the lipid is a phospholipid.

7. The formulation of claim 6 in which the phospholipid includes one or more unsaturated acyl moieties.

8. The formulation of claim 5 in which the unsaturated acyl moiety is $C_{12}$-$C_{24}$ alkenyl.

9. The formulation of claim 5 in which the unsaturated acyl moiety is $C_{16}$-$C_{20}$ alkenyl.

10. The formulation of claim 8 in which the unsaturated acyl moiety is cis n-alkenyl.

11. The formulation of claim 9 in which the unsaturated acyl moiety is cis n-alkenyl.

12. The formulation of claim 7 in which the unsaturated acyl moiety is selected from the group consisting of oleoyl, elaidoyl, myristoleoyl, palmitoleoyl, arachidonyl, linoleoyl, linolenyl, petroselinyl and erucyl.

13. The formulation of claim 7 in which the phospholipid is a phosphatidylglycerol, a phosphatidylserine, a phosphatidylethanolamine or a phosphatidic acid.

14. The formulation of claim 7 in which the phospholipid is a phosphatidylcholine.

15. The formulation claim 13 in which the unsaturated acyl moiety is selected from the group consisting of petroselinyl, erucyl, oleoyl, elaidoyl, palmitoleoyl, myristoleoyl, arachidonyl, linoleoyl, linoleny, and combinations thereof.

16. The formulation of claim 14 in which the phosphatidylcholine is dioleoylphosphatidylcholine, dielaidoylphosphatidylcholine, dipetroselinylphosphatidylcholine, dierucylphosphatidylcholine, dipalmitoleoylphosphatidylcholine, dimyristoleoylphosphatidylcholine, diarchidonylphosphatidylcholine, dilinoleoylphosphatidylcholine, dilinolenylphosphatidylcholine, or combinations thereof.

17. The formulation of claim 14 in which the phosphatidylcholine is dioleoylphosphatidylcholine.

18. The formulation of claim 1 in which the drug and the lipid are present in a ratio ranging from between about 0.05 and about 0.12 on a mole/mole basis.

19. The formulation of claim 1 in which the ratio of the drug and the lipid is about 0.10 on a mole to mole basis.

20. The formulation of claim 1 in which the bilayer is a liposome, and the liposome is a small unilamellar liposome, a large unilamellar liposome, a multilamellar liposome, or combinations thereof.

21. The formulation of claim 1 in which the lipid is dioleoylphosphatidylcholine and the 2,4-pyrimidinediamine is 22. The formulation of claim 1 in which the lipid has a loading capacity of drug in a range between about 2 mg/mL and about 8 mg/mL.

23. A method of making a liposomal formulation, comprising:

mixing at least one unsaturated amphiphilic lipid, and a 2,4-pyrimidinediamine drug selected from

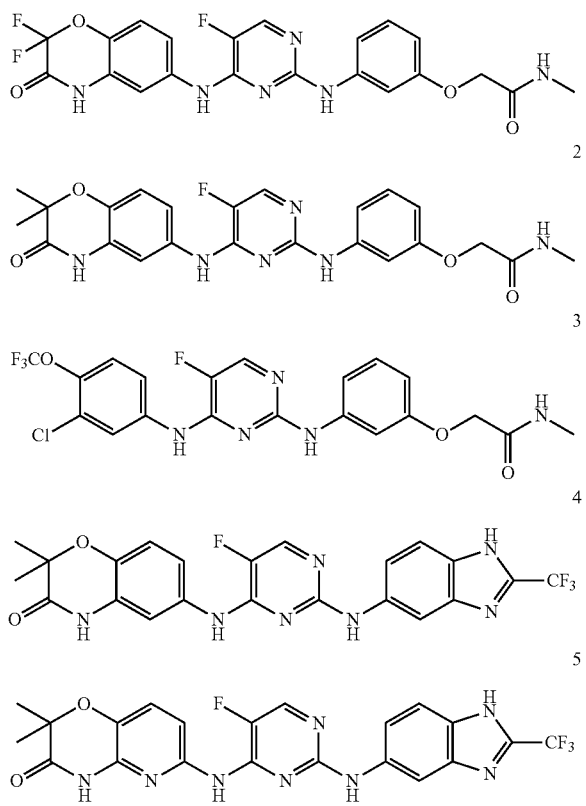

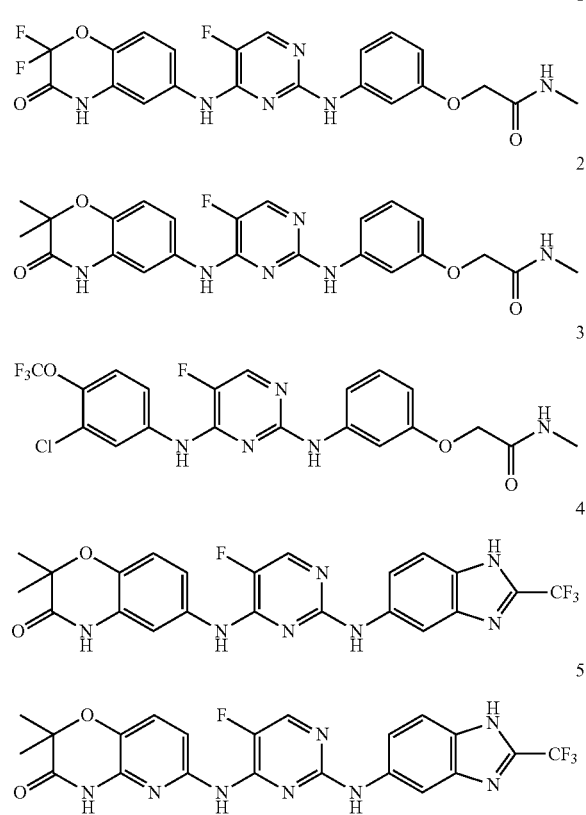

or pharmaceutically acceptable salts, hydrates, or solvates thereof, and a solvent;
  removing the solvent to form a residue comprising drug and lipid; and
  mixing the residue with water or an aqueous solution;
  wherein the drug and the lipid are present in a ratio ranging from between about 0.015 and about 0.15 on a mole/mole basis.

24. The method of claim 23 in which the mixing steps include stirring, blending, heating, shaking, agitating, sonicating, vortexing, centrifugating or combinations thereof.

25. The method of claim 23 in which the solvent is an organic solvent, a surfactant, or combinations thereof.

26. The method of claim 25 in which the organic solvent is selected from the group consisting of dichloromethane, chloroform, haloalkanes, ethers, tetrahydrofuran, acetonitrile, dimethyl sulfoxide, dimethyl formamide, alcohols, polyols, water and mixtures thereof.

27. The method of claim 25 in which the surfactant is a detergent selected from TPGS, PS 80, sodium cholate, sodium dodecylsulfate, sodium salt of N-lauroylsarcosine, lauryldimethylamine-oxide, cetyltrimethylammoniumbromide, the sodium salt of bis(2-ethylhexyl)sulfosuccinate, or combinations thereof.

28. The method of claim 23 in which the residue is a film.

29. The method of claim 23 in which the removing step includes lyophilization, vacuum evaporation, reverse phase evaporation, vacuum distillation, air drying, inert gas transfer or combinations thereof.

30. The method of claim 23 in which the aqueous solution is a buffer.

31. A liposomal formulation made by a process, comprising:
  mixing at least one unsaturated amphiphilic lipid and a 2,4-pyrimidinediamine drug selected from or pharmaceutically acceptable salts, hydrates, or solvates, thereof, and a solvent;
  removing the solvent to form a residue comprising drug and lipid; and
  mixing the residue with water or an aqueous solution;
  wherein the drug and the lipid are present in a ratio ranging from between about 0.015 and about 0.15 on a mole/mole basis.

* * * * *